(12) United States Patent
Kratz et al.

(10) Patent No.: US 9,320,803 B2
(45) Date of Patent: Apr. 26, 2016

(54) BISPHOSPHONATE-PRODRUGS

(75) Inventors: Felix Kratz, Ehrenkirchen (DE); Katrin Hochdoerffer, Kressbonn (DE)

(73) Assignee: KTB Tumorforschungsgesellschaft MBH, Freiburg im Breisgau (DE)

( * ) Notice: Subject to any disclaimer, the term of this patent is extended or adjusted under 35 U.S.C. 154(b) by 0 days.

(21) Appl. No.: 14/001,387

(22) PCT Filed: Feb. 24, 2012

(86) PCT No.: PCT/EP2012/000813
§ 371 (c)(1),
(2), (4) Date: Nov. 6, 2013

(87) PCT Pub. No.: WO2012/113571
PCT Pub. Date: Aug. 30, 2012

(65) Prior Publication Data
US 2014/0051623 A1    Feb. 20, 2014

(30) Foreign Application Priority Data

Feb. 24, 2011    (EP) ..................... 11001551

(51) Int. Cl.
| | | |
|---|---|---|
| A61K 38/00 | (2006.01) | |
| A61K 47/00 | (2006.01) | |
| A01N 43/04 | (2006.01) | |
| A61K 31/70 | (2006.01) | |
| A01N 43/00 | (2006.01) | |
| A61K 31/33 | (2006.01) | |
| A01N 43/64 | (2006.01) | |
| A61K 31/41 | (2006.01) | |
| A01N 43/36 | (2006.01) | |
| A61K 31/40 | (2006.01) | |
| A01N 43/16 | (2006.01) | |
| A61K 31/35 | (2006.01) | |
| C07H 15/24 | (2006.01) | |
| C07D 345/00 | (2006.01) | |
| A61K 47/48 | (2006.01) | |
| C07K 5/062 | (2006.01) | |
| C07K 5/078 | (2006.01) | |
| C07D 405/00 | (2006.01) | |
| C07H 15/252 | (2006.01) | |
| A61K 31/704 | (2006.01) | |
| A61P 19/08 | (2006.01) | |
| A61P 35/00 | (2006.01) | |

(52) U.S. Cl.
CPC .......... *A61K 47/48084* (2013.01); *A61K 31/35* (2013.01); *A61K 31/40* (2013.01); *A61K 31/704* (2013.01); *A61K 47/48338* (2013.01); *C07D 405/00* (2013.01); *C07H 15/252* (2013.01); *C07K 5/06026* (2013.01); *C07K 5/06052* (2013.01); *C07K 5/06139* (2013.01); *A61K 38/00* (2013.01)

(58) Field of Classification Search
None
See application file for complete search history.

(56) References Cited

U.S. PATENT DOCUMENTS 8,778,914 B2 * 7/2014 Kratz et al. .................. 514/141

FOREIGN PATENT DOCUMENTS

| WO | 94/06750 A1 | 3/1994 |
| WO | 2007/096703 A2 | 8/2007 |
| WO | 2009/083614 A1 | 7/2009 |
| WO | 2011/023367 A2 | 3/2011 |

OTHER PUBLICATIONS

Erez et al., "Chemotherapeutic bone-targeted bisphosphonate prodrugs with hydrolytic mode of activation," Bioorgan. Med. Chem. Lett. 18:816-820 (2008).*
Scott et al., Bioorgan. Med. Chem. Lett. 6:1491-1496 (1996).*
"Oxygen Family" available online at http://www.learner.org/interactives/periodic/groups6.html, 1 page (first available 2008).*
Thornber, C. W., "Isosterism and Molecular Modification in Drug Design," Chem. Soc. Rev., 1957, vol. 8, pp. 563-580.*
Bauss, F., et al., "Effect of 17β-Estradiol-Bisphosphonate Conjugates, Potential Bone-Seeking Estrogen Pro-Drugs, on 17β-Estradiol Serum Kinetics and Bone Mass in Rats," Calcif Tissue Int., 1996, vol. 59, pp. 168-173.
Erez, Rotem, et al., "Chemotherapeutic Bone-Targeted Bisphosphonate Prodrugs with Hydrolytic Mode of Activation," Bioorganic & Medicinal Chemistry Letters, 2008, vol. 18, pp. 816-820.
Zhang, Sufeng, et al., "Cleavage of Disulfide-Linked Fetuin-Bisphosphonate Conjugates with Three Physiological Thiols," Biomacromolecules, 2005, vol. 6, pp. 2800-2808.
Hirabayashi, H., Relationship Between Physicochemical and Osteotropic Properties of Bisphosphonic Derivatives: Rational Design for Osteotropic Drug Delivery System (ODDS), Pharmaceutical Research, Jan. 30, 2001, vol. 18 (5), pp. 646-651.

* cited by examiner

*Primary Examiner* — James H Alstrum Acevedo
*Assistant Examiner* — Thea D'Ambrosio
(74) *Attorney, Agent, or Firm* — McDonnell Boehnen Hulbert & Berghoff LLP

(57) ABSTRACT

The present invention relates to a prodrug, comprising a pharmaceutically and/or diagnostically active compound, and one or more bisphosphonate groups, to a process for producing such a prodrug, and to a pharmaceutical composition comprising said prodrug, to be used for the treatment of bone-related disorders such as bone cancer.

1 Claim, 5 Drawing Sheets

Fig. 1
Chromatogramme of 14 at pH 7.1 (t = 0 h); ret. time: 3.9 min
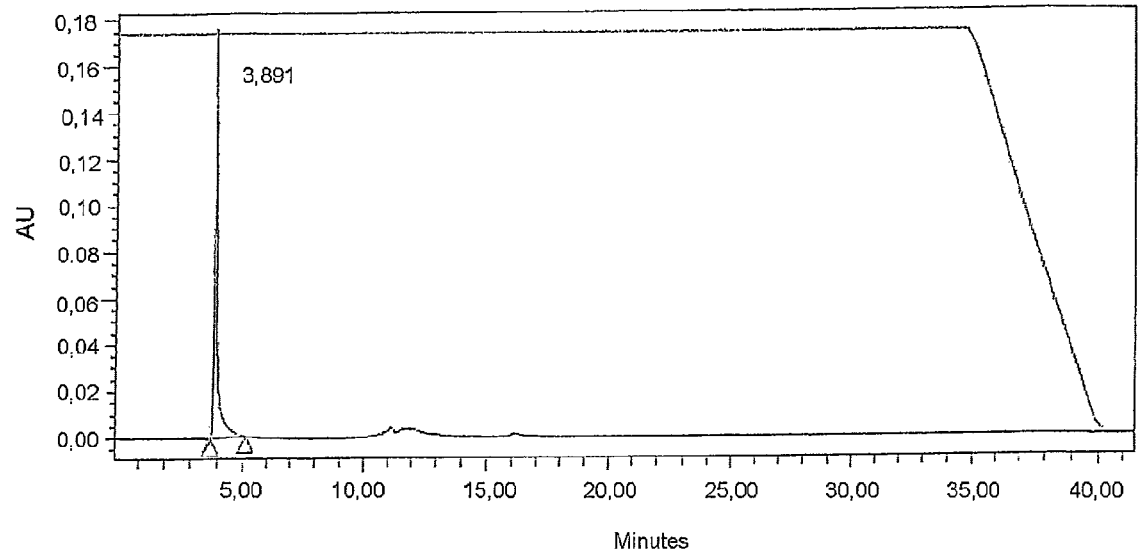
Fig. 1A
Chromatogramme of 14 at pH 3.8 (t = 5 min); ret. time: 10.8 min
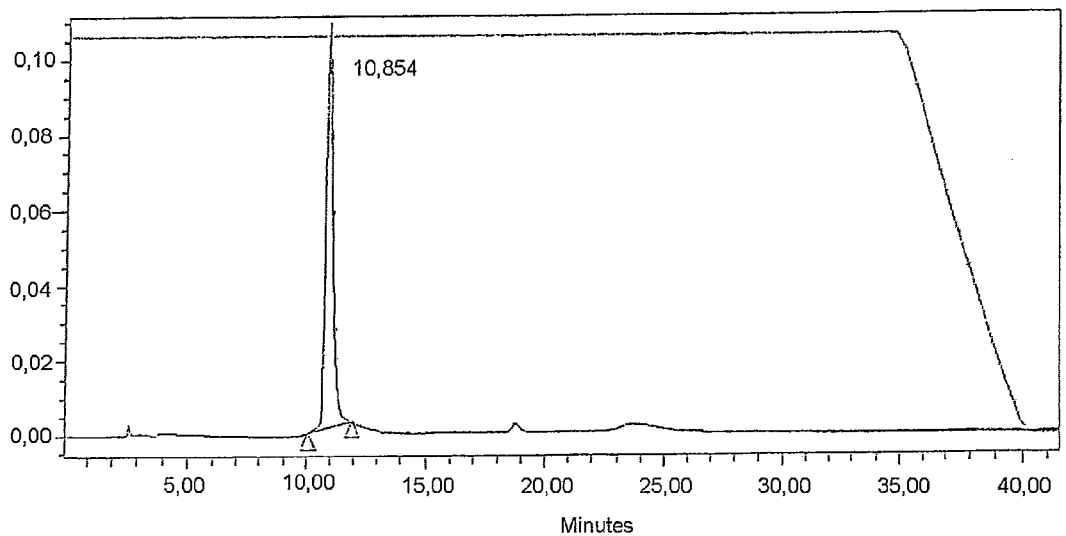
Fig. 1B Chromatogramme of doxorubicin; ret. time: 11.2 min
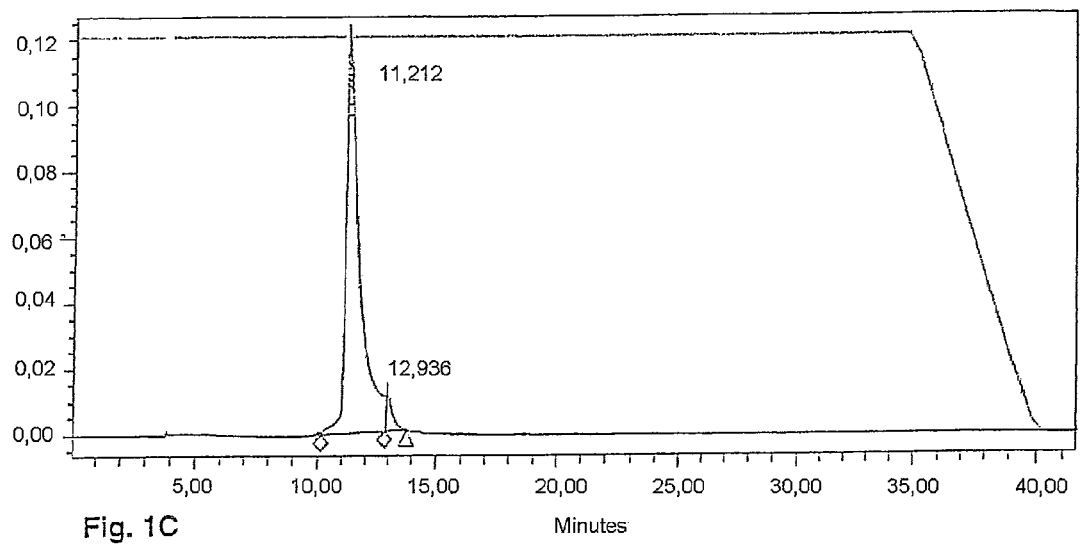
Fig. 1C
Fig. 2
Chromatogramme of 16 with cathepsin B (t = 0 h); ret. time: 45.7 min, impurity at 30. 3 min
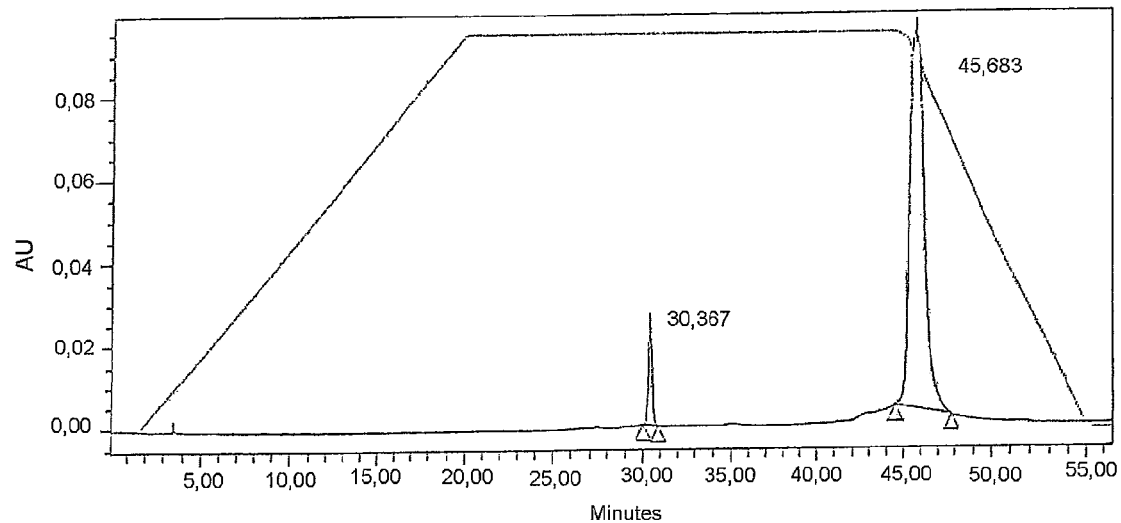
Fig. 2A Chromatogramme of 16 with cathepsin B (t = 1 h); ret. time: 26.7 min corresponding to doxorubicin (see Fig. 2 C for chromatogramme of doxorubicin reference)

Chromatogramme of doxorubicin; ret. time: 26.7 min

SEQUENCE LISTING

<160> NUMBER OF SEQ ID NOS: 10

<210> SEQ ID NO 1
<211> LENGTH: 4
<212> TYPE: PRT
<213> ORGANISM: Artificial Sequence

```
<220> FEATURE:
<223> OTHER INFORMATION: Preferred peptide sequence incorporated in the
      prodrug

<400> SEQUENCE: 1

Ala Leu Ala Leu
1

<210> SEQ ID NO 2
<211> LENGTH: 6
<212> TYPE: PRT
<213> ORGANISM: Artificial Sequence
<220> FEATURE:
<223> OTHER INFORMATION: Preferred peptide sequence incorporated in the
      prodrug

<400> SEQUENCE: 2

Ser Ser Tyr Tyr Ser Arg
1               5

<210> SEQ ID NO 3
<211> LENGTH: 6
<212> TYPE: PRT
<213> ORGANISM: Artificial Sequence
<220> FEATURE:
<223> OTHER INFORMATION: cleavable linker

<400> SEQUENCE: 3

Ser Ser Tyr Tyr Ser Leu
1               5

<210> SEQ ID NO 4
<211> LENGTH: 7
<212> TYPE: PRT
<213> ORGANISM: Artificial Sequence
<220> FEATURE:
<223> OTHER INFORMATION: Preferred peptide sequence incorporated in the
      prodrug

<400> SEQUENCE: 4

Arg Ser Ser Tyr Tyr Ser Leu
1               5

<210> SEQ ID NO 5
<211> LENGTH: 8
<212> TYPE: PRT
<213> ORGANISM: Artificial Sequence
<220> FEATURE:
<223> OTHER INFORMATION: Preferred peptide sequence incorporated in the
      prodrug

<400> SEQUENCE: 5

Phe Pro Lys Phe Phe Ser Arg Gln
1               5

<210> SEQ ID NO 6
<211> LENGTH: 8
<212> TYPE: PRT
<213> ORGANISM: Artificial Sequence
<220> FEATURE:
<223> OTHER INFORMATION: Preferred peptide sequence incorporated in the
      prodrug
<220> FEATURE:
<221> NAME/KEY: nph
<222> LOCATION: (6)..(6)
<223> OTHER INFORMATION: x = nitrophenylalanine

<400> SEQUENCE: 6
```

```
Lys Pro Ile Glu Phe Xaa Arg Leu
1               5

<210> SEQ ID NO 7
<211> LENGTH: 8
<212> TYPE: PRT
<213> ORGANISM: Artificial Sequence
<220> FEATURE:
<223> OTHER INFORMATION: Preferred peptide sequence incorporated in the
      prodrug

<400> SEQUENCE: 7

Gly Pro Leu Gly Ile Ala Gly Gln
1               5

<210> SEQ ID NO 8
<211> LENGTH: 5
<212> TYPE: PRT
<213> ORGANISM: Artificial Sequence
<220> FEATURE:
<223> OTHER INFORMATION: Preferred peptide sequence incorporated in the
      prodrug

<400> SEQUENCE: 8

Gly Gly Gly Arg Arg
1               5

<210> SEQ ID NO 9
<211> LENGTH: 8
<212> TYPE: PRT
<213> ORGANISM: Artificial Sequence
<220> FEATURE:
<223> OTHER INFORMATION: Preferred peptide sequence incorporated in the
      prodrug

<400> SEQUENCE: 9

Gly Pro Gln Gly Ile Trp Gly Gln
1               5

<210> SEQ ID NO 10
<211> LENGTH: 4
<212> TYPE: PRT
<213> ORGANISM: Artificial Sequence
<220> FEATURE:
<223> OTHER INFORMATION: Preferred peptide sequence incorporated in the
      prodrug

<400> SEQUENCE: 10

Gly Phe Leu Gly
1
```

BISPHOSPHONATE-PRODRUGS

CROSS REFERENCE TO RELATED APPLICATIONS

The present application is a 35 U.S.C. 371 National Application of PCT/EP2012/000813, filed Feb. 24, 2012, which claims priority to European Patent Application No. EP11001551, filed Feb. 24, 2011.

The present invention relates to a prodrug, comprising a pharmaceutically and/or diagnostically active compound, and one or more bisphosphonate groups, to a process for producing such a prodrug, and to a pharmaceutical composition comprising said prodrug, to be used for the treatment of bone-related disorders such as bone cancer including metastases.

Healthy bones keep being restructured during their whole lives; about 8% of the entire skeleton is renewed every year. Bone formation and resorption, the so-called remodeling, are in balance and are characteristic of the fully developed bone, bone-forming cells (osteoblasts) and bone-resorbing cells (osteoclasts) taking part in said process. The resorption in bone restructuring starts with binding of the ruffled border of the osteoclasts, an extensive cell membrane, to the bone surface. After surface contact, lysosomal enzymes (e.g. acidic phosphatase or cathepsins) and matrix metalloproteases are secreted, and an ATP-dependent ion pump reduces the pH value in the bone troughs that form the so-called resorption lacunas. At the end of the resorption phase, the osteoclasts are released from the bone surface and osteoblasts or the progenitor cells thereof settle in the lacunae and initiate bone formation.

Bone disorders are characterized by an imbalance between bone formation and bone resorption. For example, when malignant diseases progress, it often happens that micrometastases form, which are often not found in the primary diagnosis. Most commonly, metastases are formed in the liver, in the lungs and in the bones. The symptoms of bone metastasis are serious. In particular, due to the growth of the metastases in the bone marrow, the surrounding bone substance is affected. On the one hand, this is due to pressure damage. On the other hand, the tumor cells secrete substances that change the natural balance between bone formation and bone resorption in the tumor area and thus destroy the bone substance. These processes often result in pain and may finally cause bone fractures that heal very badly. If the spine is affected, there is the additional risk of nerves or the bone marrow itself being crushed due to the collapse of the vertebral bodies. This may lead to symptoms of paralysis and sensation disorders. Moreover, in many cases, the result is a flooding of the blood with calcium, a so-called hypercalcemia.

Bone metastases settle in areas with high blood flow and pronounced remodeling, where growth factors and proteases facilitate the proliferation and invasion of the tumor cells. They are radiographically classified as osteoblastic or osteolytic, which result due to an imbalance between bone formation by osteoblasts and bone resorption by osteoclasts. In addition to the osteoblasts and osteoclasts, bone metastases consist of fibroblasts, macrophages, endothelial cells and the tumor cells of the respective metastasized primary tumor, which together secrete a number of growth factors and proteases, in particular matrix metalloproteases, cathepsins and urokinase, which initiate and promote bone metastasis.

The current treatment of bone metastases is palliative and is based on a combination of chemotherapy, pain therapy and the use of bisphosphonates. The treatment with bisphosphonates reduces the incidence of bone fractures and bone pain and thus improves the quality of life, however without increasing the survival time of the patients. In order to improve the palliative and therapeutic options, new therapeutic approaches are urgently required.

One promising therapeutic approach is bone targeting. In particular, the most striking feature of bone tissue is the mineralized, extracellular matrix with a mineral percentage of about 70% by weight, which primarily consists of apatite $Ca_{10}(PO_4)_6X_2$ wherein X is fluoride (fluorapatite), hydroxy (hydroxyapatite) or chloride (chlorapatite). Moreover, the organic matrix accounts for about 20% by weight and water for about 10% by weight.

In the past, bisphosphonates, tetracyclines, polymalonates and polyaspartates, as well as sialic acid were proposed as osteotropic ligands for bone targeting, wherein the substance class of the bisphosphonates has been best examined.

Bisphosphonates are derivatives of pyrophosphate, in which the central and hydrolytically unstable P—O—P bond is replaced by a stable P—C—P bond.

Bisphosphonates lead to an inactivation of osteoclasts, but other mechanisms of action are postulated as well, e.g. the inhibition of the farnesyl-pyrophosphate synthase or of the matrix metalloproteases. The affinity between the bisphosphonates and the bone apatite is very high.

Also bisphosphonate derivatives with anti-tumor agents such as bisphosphonate complexes of cisplatin analogues and bisphosphonate derivatives of methotrexate have been developed. However, for bisphosphonate complexes of cisplatin analogues significantly higher dosages compared to cisplatin are required. Moreover, the methotrexate bisphosphonate derivative shows a pronounced systemic toxicity.

WO-A-2007/092338 discloses compositions comprising a bisphosphonate and an antifolate. Moreover, WO-A-2008/077241 discloses phosphonated glycopeptides and lipoglycopeptide antibiotics and their use in the treatment of bone and joint infections. WO-A-02/083150 and U.S. Pat. No. 6,214,812 describe bisphosphonate conjugates. However, all of these documents fail to address a prodrug system which is capable of releasing a pharmaceutically active compound selectively at the desired site of action, namely in/on the bone.

Thus, the technical problem underlying the present invention is to provide a target-directed prodrug for the treatment of bone-related disorders such as bone cancer including bone metastases, which should exhibit a more efficient release of a pharmaceutically and/or diagnostically active compound in the bone, and which should exhibit a reduced systemic toxicity as compared to the free pharmaceutically and/or diagnostically active compound, thus leading to less side effects.

According to the present invention, the above technical problem is solved by providing a prodrug which comprises (a) a pharmaceutically and/or diagnostically active compound; (b) a cleavable linker which is bound to the pharmaceutically and/or diagnostically active compound; (c) a spacer group which is bound to the cleavable linker; and (d) one or more bisphosphonate groups which are bound to the spacer group, wherein at least one of the one or more bisphosphonate groups has the following structure (IIc):

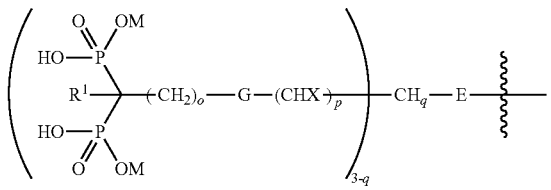

(IIc)

wherein
o is an integer independently selected from 0 to 12,
p is an integer independently selected from 0 to 2,
q is an integer independently selected from 0 to 2,
X is selected from the group consisting of F, Cl, Br, I, $NO_2$, $SO_3H$, CN, OH, COOH, $COOCH_3$, —CHO, —$CHOCH_3$, an $C_{1-8}$ alkyl group and an $C_{1-6}$ aryl group,
$R^1$ may be the same or different and is independently selected from the group consisting of H, F, Cl, Br, I, $NO_2$, CN, $COOCH_3$, —CHO, —$CHOCH_3$, an $C_{1-8}$ alkyl group and an $C_{1-6}$ aryl group,
E represents O, NH, a carbon-carbon single bond, a carbon-carbon double bond or a carbon-carbon triple bond,
M is independently selected from hydrogen, sodium, potassium, calcium, magnesium, ammonium and 2-ammonium-2-hydroxymethyl-propane-1,3-diol, and
G represents S, O, NH, a carbon-carbon single bond, a carbon-carbon double bond or a triazole moiety, preferably S.

In particular, the structure of the prodrug according to the present invention can also be represented by the following structure, wherein a pharmaceutically and/or diagnostically active compound (a) is bound to a cleavable linker (b), which is bound to a spacer group (c), which is bound to one or more bisphosphonate groups (d), as defined above:

The prodrug according to the present invention is particularly suitable for the treatment of bone-related disorders such as bone cancer including metastases. The prodrug according to the present invention is designed to release the pharmaceutically and/or diagnostically active compound in bone metastases exploiting the acidic environment or the expression of specific enzymes in bone metastases. In particular, bone metastases are characterized by a decreased pH value and by overexpression of specific proteases. The most important proteases overexpressed in bone metastasis are the matrix metalloproteases, the ADMAPs (disintegrin and metalloproteinases), cathepsin B and K and uPA (urokinase-plasminogen activator) as well as tPA (tissue-plasminogen activator) (J. K. Woodward, I. Holen, R. E. Coleman, D. J. Buttle, *Bone* 2007, 41, 912).

Moreover, in order to disintegrate the apatite matrix during bone remodeling and bone metastasis, the pH value must be decreased with respect to the physiological pH value. The pH value in the resorption lacunas is in the acidic range. The pH gradient is ensured by provision of $H^+$ ions by carbonic anhydrase type II, which are transported out of the osteoclasts via the ruffled border by means of an ATP ion pump. By acidification of the extracellular milieu, lysosomally secreted proteases, such as cathepsin B and K, have an ideal milieu for their proteolytic activity. In addition to an overexpression of matrix metalloproteases and ADMAPs (disintegrin and met-alloproteinases) in bone metastases, the expression of the urokinase-plasminogen activator (uPA) correlates with the formation of bone metastases.

The pharmaceutically and/or diagnostically active compound (a) is preferably selected from the group consisting of a cytostatic agent, a cytotoxic agent, a cytokine, an immunosuppressant, an antirheumatic, an antiphlogistic, an antibiotic, an analgesic, a virostatic, and an antimycotic agent, a transcription factor inhibitor, a cell cycle modulator, a MDR modulator, a vascular disrupting agent, a proteasome or protease inhibitor, a protein kinase inhibitor, an apoptosis modulator, an enzyme inhibitor, an angiogenesis inhibitor, a hormone or hormone derivative, a radioactive substance, a light emitting substance, and a light absorbing substance.

In view of an application of the prodrug as an anti-tumor agent, it is preferred that the pharmaceutically and/or diagnostically active compound is a cytostatic agent selected from the group consisting of N-nitrosoureas, the anthracyclines doxorubicin, 2-pyrollinoanthracycline, morpholinoanthracycline, diacetatoxyalkylanthracycline, daunorubicin, epirubicin, idarubicin, mitoxantrone and ametantrone, and any derivatives thereof; the alkylating agents chlorambucil, bendamustine, melphalan, and oxazaphosphorines, and any derivatives thereof; the antimetabolites 5-fluorouracil, 2'-deoxy-5-fluorouridine, cytarabine, cladribine, fludarabine, pentostatine, gemcitabine, 6-thioguanine and 6-mercaptopurine, and any derivatives thereof; the folic acid antagonists methotrexate, raltitrexed, pemetrexed and plevitrexed, the taxanes paclitaxel and docetaxel, and any derivatives thereof; the camptothecins topotecan, irinotecan, SN-38, 10-hydroxy-camptothecin, GG211, lurtotecan, 9-aminocamptothecin and camptothecin, and any derivatives thereof; the *Vinca* alkaloids vinblastine, vincristine, vindesine and vinorelbine, and any derivatives thereof; calicheamicins and any derivatives thereof; maytansinoids and any derivatives thereof; auristatins and any derivatives thereof; epothilones and any derivatives thereof; duocarmycins and any derivatives thereof; bleomycin, dactinomycin, plicamycin, mitomycin C and cis-configured platinum(II) complexes.

In order to be bound to the cleavable linker (b), the pharmaceutically and/or diagnostically active compound (a) may be derivatized. Accordingly, in order to contain a suitable moiety for chemical derivatization, the pharmaceutically and/or diagnostically active compound to be used to prepare the prodrug of the present invention may contain at least one functional group selected from —COOH, —OH, —$NH_2$, —NH—$NH_2$, —CO—NH—$NH_2$, —$SO_3H$, —SH or a carbonyl group.

According to the present invention, the cleavable linker (b) comprises a group which can be cleaved. Said cleavage preferably takes place at the desired site of action, e.g. in bones, in particular in bone metastases. Since bone metastases are characterized by a decreased pH value and by overexpression of specific enzymes, it is preferred that the cleavable linker comprises a group which can be cleaved enzymatically and/or pH-dependently. For example, the cleavable linker of the prodrug of the present invention may contain at least one peptide bond which is preferably located within a cleavable peptide sequence of a protease. A peptide bond can therefore be implemented by the insertion of a respective peptide sequence into the cleavable linker. Suitable enzymes are, for example, proteases and peptidases, e.g. matrix metalloproteases (MMP), cysteine proteases, serine proteases and plasmin activators, which are formed or activated in intensified manner in diseases such as rheumatoid arthritis or cancer, leading to excessive tissue degradation, inflammations and metastasis. Preferred examples of enzymes are the metalloproteases, the ADMAPs (disintegrin and metalloproteinases), cathepsin B and K and uPA (urokinase-plasminogen activator) as well as tPA (tissue-plasminogen activator), since these enzymes are generally overexpressed in bone metastases.

In a preferred embodiment of the present invention, the cleavable linker comprises an enzymatically cleavable peptide sequence selected from the group consisting of -Arg-, -Arg-Arg-, -Phe-Arg-, -Phe-Cit-, -Ile-Pro-Lys-, -Lys-, -Lys-Lys-, -Arg-Lys-, -Leu-Arg-, -Phe-Arg-, -Val-Arg-, -Ala-Leu-Ala-Leu- (SEQ ID NO:1), -Phe-Lys-, -Phe-Lys-Ala-, -Val-Cit-, -Val-Ala-, -Val-Arg-, -Ala-Phe-Lys-, -D-Ala-Phe-Lys-, -Ser-Ser-Tyr-Tyr-Ser-Arg- (SEQ ID NO:2), -Ser-Ser-Tyr-Tyr-Ser-Leu- (SEQ ID NO:3), -Arg-Ser-Ser-Tyr-Tyr-Ser-Leu- (SEQ ID NO:4), -Phe-Pro-Lys-Phe-Phe-Ser-Arg-Gln- (SEQ ID NO:5), -Lys-Pro-Ile-Glu-Phe-Xaa-Arg-Leu- (SEQ ID NO:6), -Gly-Pro-Leu-Gly-Ile-Ala-Gly-Gln- (SEQ ID NO:7), -Gly-Pro-Gln-Gly-Ile-Trp-Gly-Gln- (SEQ ID NO:9), -Gly-Phe-Leu-Gly- (SEQ ID NO:10), -Gly-Gly-, -Gly-Gly-Gly- and -Gly-Gly-Gly-Arg-Arg- (SEQ ID NO:8).

In another preferred embodiment of the present invention, the cleavable linker comprises an acid-sensitive group which can be cleaved upon a decrease in the pH-value. Preferably, this acid-sensitive group contains at least one acid-sensitive bond. It is particularly preferable that the acid-sensitive group is selected from ester, acetal, ketal, imine, aconityl, hydrazone, acylhydrazone and sulfonylhydrazone bonds or bonds containing a trityl group. Because bone metastases are generally characterized by a decreased pH value, such acid-sensitive groups can be cleaved at the desired site, namely the metastasis.

In order to release the pharmaceutically and/or diagnostically active compound, the cleavable group is cleaved at the desired site of action, thus setting free the pharmaceutically and/or diagnostically active compound. The cleavable linker (b) may further contain one or more self-immolative groups which produce, after peptide cleavage or cleavage of an acid-sensitive bond, a labile self-immolative spacer drug derivative that in turn hydrolyzes in a spontaneous reaction and releases the pharmaceutically and/or diagnostically active compound. Preferably, the cleavable linker comprises a self-immolative group which is selected from one of the following groups:

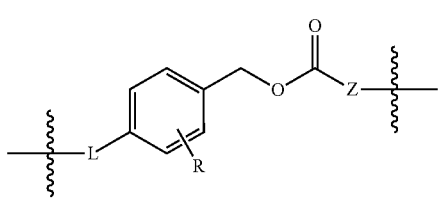

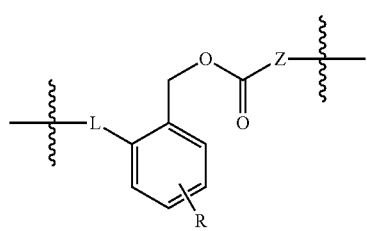

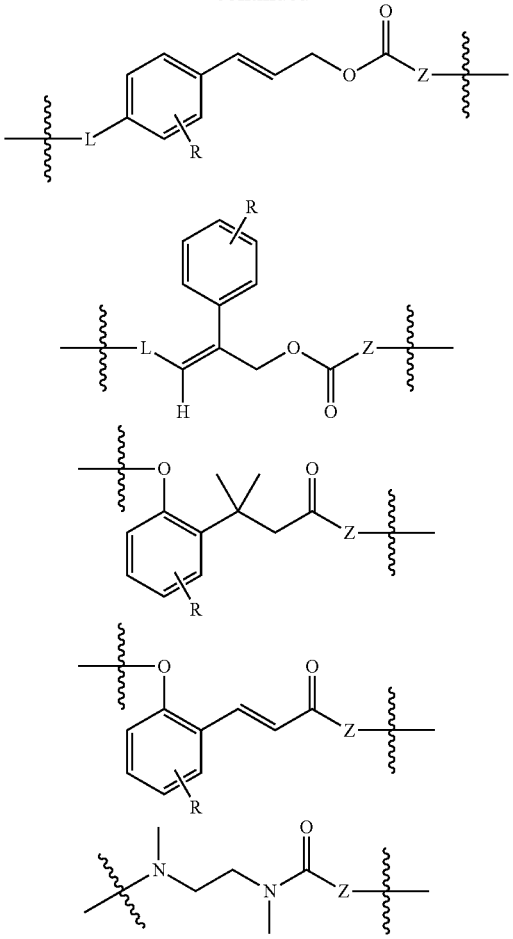

wherein the pharmaceutically and/or diagnostically active compound (a) is bound to the Z-terminus of the self-immolative group, wherein Z and L are independently selected from O, S and NH, and R represents one or more substituents at the phenyl ring which are independently selected from the group consisting of F, Cl, Br, I, $NO_2$, CN, OH, a $C_{1-8}$ alkyl group and a $C_{1-6}$ aryl group.

Moreover, the prodrug according to the present invention further comprises a spacer group (c) which is bound to the cleavable linker (b). This group may have the function as a mere spacer, but also to enhance water-solubility, bio-compatibility and/or molecular mass of the prodrug. Moreover, the spacer group (c) can also be present only for synthetic reasons, namely to enable a connection of the cleavable linker (b) to the one or more bisphosphonate groups (d) by a convenient synthetic route. Accordingly, the spacer group (c) is not restricted and may comprise any groups which enable a convenient connection of the cleavable linker (b) to the one or more bisphosphonate groups (d).

The spacer group (c) may be bound to the one or more bisphosphonate groups (d) for example through an amide bond, an ester bond, an ether bond, a thioether bond, a disulfide bond, or a carbon-carbon single bond, a carbon-carbon double bond or a carbon-carbon triple bond.

For example, the spacer group (c) may comprise a unit obtained from the group consisting of a maleinimide group, a halogenacetamide group, a halogenacetate group, a pyridylthio group, a vinyl carbonyl group, an aziridin group, a N-hydroxysuccinimide ester group, a disulfide group, and a substituted or unsubstituted acetylene group. In particular, after addition of a suitable reagent, the above groups may have the following exemplarily shown structures, wherein Z may be O, S or NH:

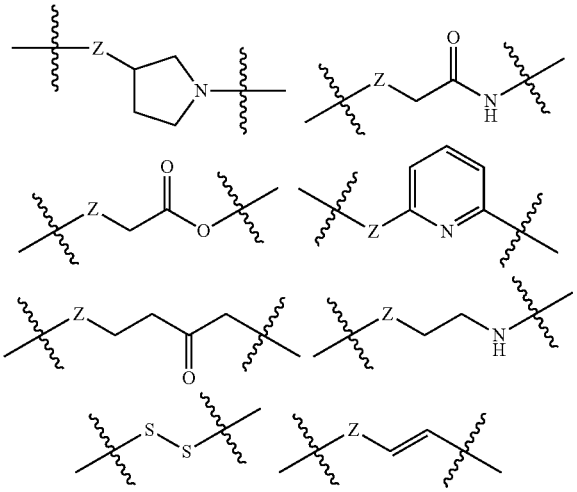

In a further preferred embodiment of the present invention, the spacer group (c) may also comprise an aliphatic chain —$(CH_2)_n$— with n being an integer of from 1 to 12, an oligoethylene glycol —$(O—CH_2—CH_2)_n$— with n being an integer of from 1 to 12, a synthetic poly(ethylene glycol), or a phenyl ring, optionally substituted with one or more substituents selected from the group consisting of F, Cl, Br, I, $NO_2$, $SO_3H$, CN, OH, COOH, a $C_{1-8}$ alkyl group and a $C_{1-6}$ aryl group, or combinations thereof. It is particularly preferred that the spacer group contains a synthetic polymer selected from the group consisting of poly(ethylene glycol) (PEG), monomethoxy PEG (mPEG), polyglycerol (PG), poly(ethylene imine) (PEI) and N-(2-hydroxypropyl)methacrylamide (HPMA) copolymers, and combinations thereof. It is particularly preferable that the spacer group comprises PEG having a mass e.g. ranging from 1,000 to 50,000 Da. It is more preferred that the PEG has a mass in the range of from 2,000 to 20,000 Da. Examples of such spacer groups can be derived from commercially available protected mercapto derivatives of PEG of the following structure SuOOC—$CH_2$—$CH_2$-PEG-$CH_2$—$CH_2$—S-Trt. This group can be converted into a unit for the spacer group having the structure —OOC—$CH_2$—$CH_2$-PEG-$CH_2$—$CH_2$—S—.

The above linker groups may be advantageous from the viewpoint of an efficient synthesis of the prodrug. Moreover, the synthetic polymer may be advantageous from the viewpoint of enhancing water-solubility, bio-compatibility, molecular mass and biodistribution of the prodrug.

According to the present invention, the prodrug comprises one or more bisphosphonate groups (d) which are bound to the spacer group, wherein at least one, preferably all, of the one or more bisphosphonate groups has the structure of above formula (IIc). In a preferred embodiment of the present invention, the prodrug contains 1 to 12 bisphosphonate groups. It is particularly preferred that the prodrug contains one, two or three bisphosphonate groups. If the prodrug contains more than one bisphosphonate group, the bisphosphonate groups, other than the bisphosphonate group according to formula (IIc), can be selected from any suitable bisphosphonate groups. In a preferred embodiment of the present invention, the bisphosphonate groups, other than the bisphosphonate group according to formula (IIc), are independently selected from the group consisting of etidronate, clodronate, tiludronate, pamidronate, 1-amino-1,1-diphosphonate methane (aminoBP), risedronate, ibandronate, 1-hydroxy ethylidene-1,1-diphosphonic acid (HEDP), alendronate and zoledronate. The above bisphosphonates may be chemically modified in such a manner that they can be attached to the spacer group. In a particularly preferred embodiment of the present invention, the bisphosphonate group is pamidronate.

In another preferred embodiment, the bisphosphonate groups (d), beside the bisphosphonate group according to formula (IIc), have independently one of the following structures (IIa) to (Va), (IIb) to (Vb):

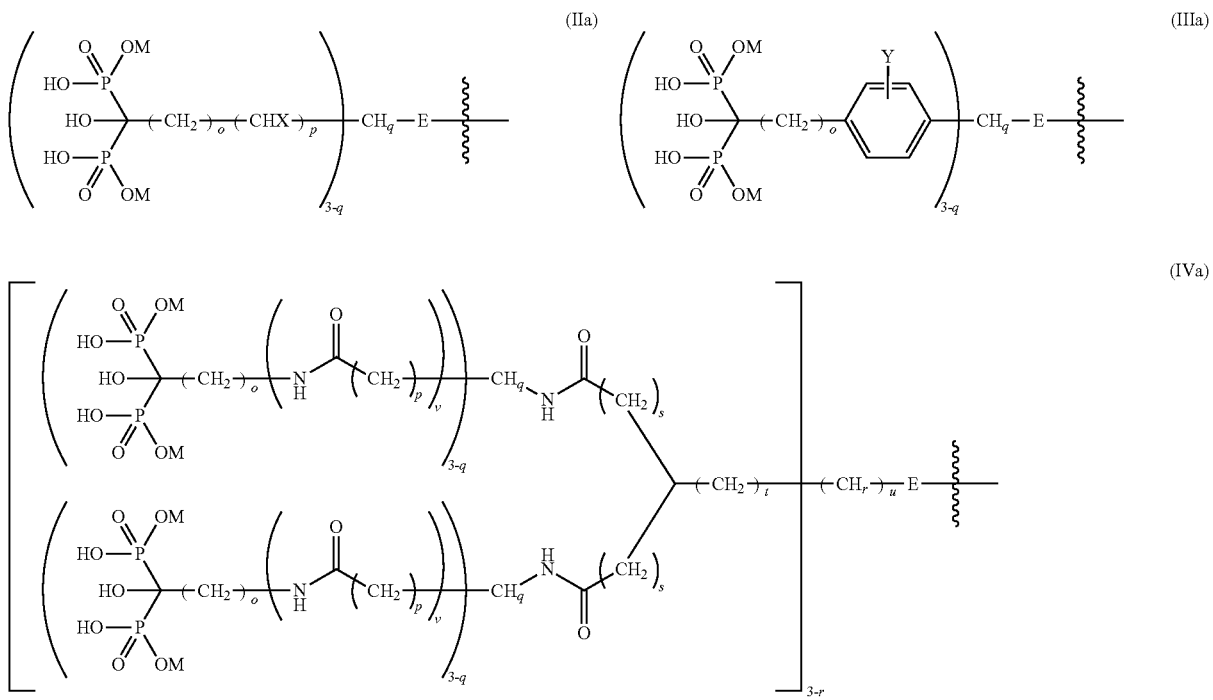

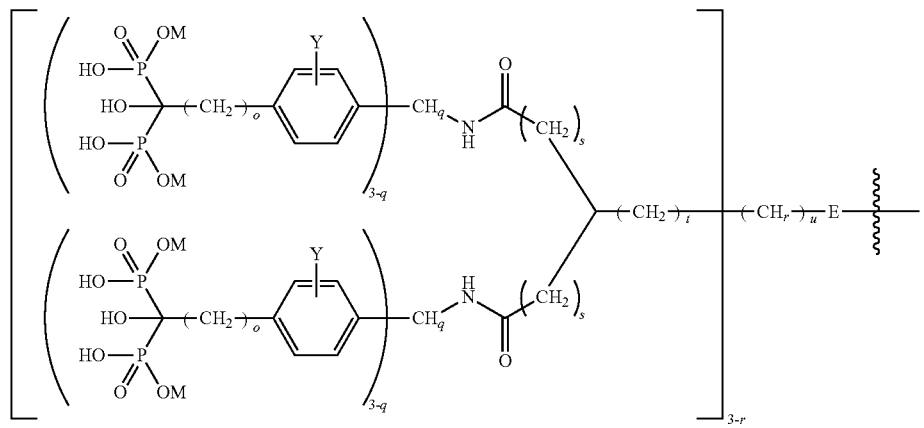

(Va)

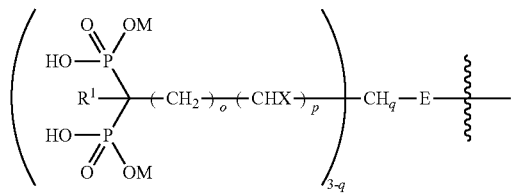

(IIb)

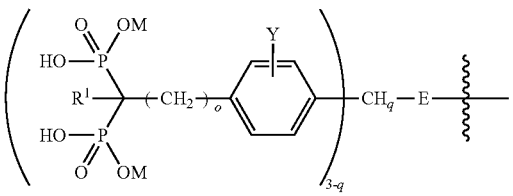

(IIIb)

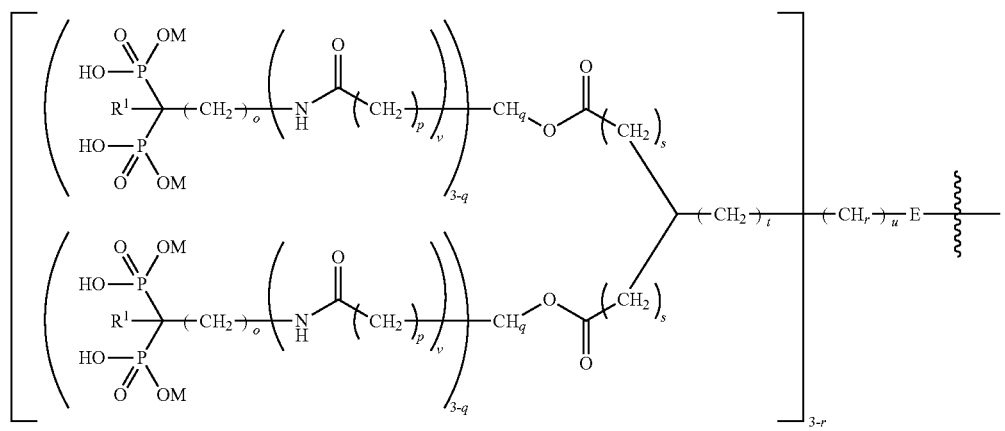

(IVb)

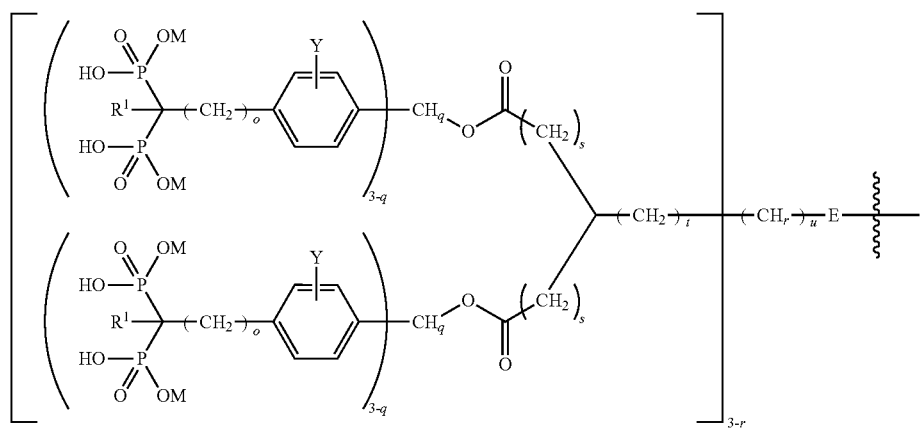

(Vb)

wherein
o is an integer independently selected from 0 to 12,
p is an integer independently selected from 0 to 2,
q is an integer independently selected from 0 to 2,
r is an integer independently selected from 1 or 2,
s an integer independently selected from 0 to 12,
t is an integer independently selected from 0 to 2,
u is an integer independently selected from 0 or 1,
v is an integer independently selected from 0 to 2, each of X and Y are independently selected from the group consisting of F, Cl, Br, I, $NO_2$, $SO_3H$, CN, OH, COOH, $COOCH_3$, —CHO, —$CHOCH_3$, an $C_{1-8}$ alkyl group and an $C_{1-6}$ aryl group, $R^1$ may be the same or different and is independently selected from the group consisting of H, F, Cl, Br, I, $NO_2$, CN, $COOCH_3$, —CHO, —$CHOCH_3$, an $C_{1-8}$ alkyl group and an $C_{1-6}$ aryl group, E represents O, NH, a carbon-carbon single bond, a carbon-carbon double bond or a carbon-carbon triple bond, and M is independently selected from hydrogen, sodium, potassium, calcium, magnesium, ammonium and 2-ammonium-2-hydroxymethyl-propane-1,3-diol.

According to the present invention, the different components (a), (b), (c) and (d) can be arbitrarily combined without any restrictions, to give the prodrug of the present invention.

In a preferred embodiment of the present invention, the prodrug has the following general formula (I):

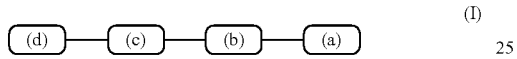

(I)

wherein the unit (d) represents the one or more bisphosphonate groups having one of the above structures (II) to (V) as defined above, wherein the unit (c) represents the spacer group, wherein the unit (b) represents the cleavable linker, and wherein the unit (a) represents the pharmaceutically and/or diagnostically active compound.

In the above prodrug of general formula (I), if more than one bisphosphonate group are present, the unit (d), beside the bisphosphonate group according to formula (IIc), may contain one of the following structures (VIa) to (VIIIa) or (VIb) to (VIIIb):

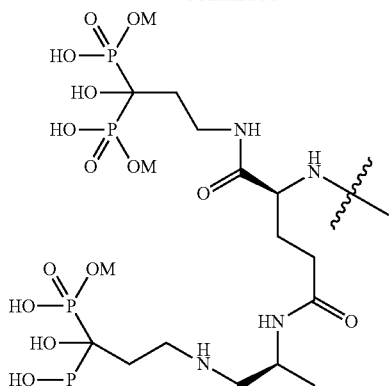

(VIa)

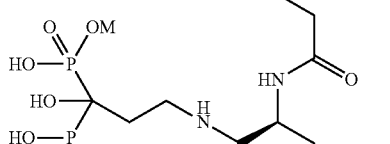

(VIIa)

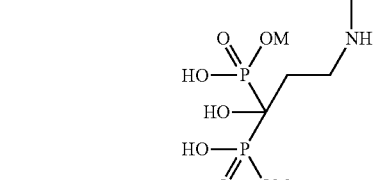

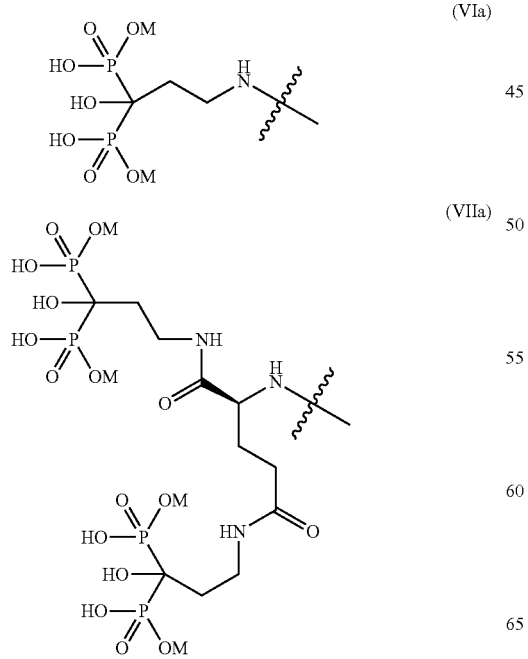

-continued (VIIIa)

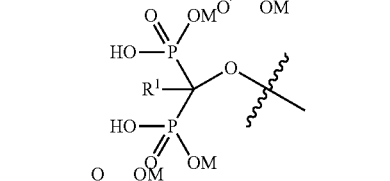

(VIb)

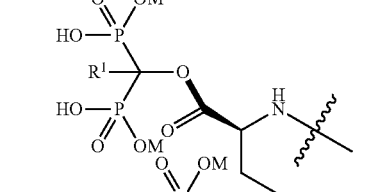

(VIIb)

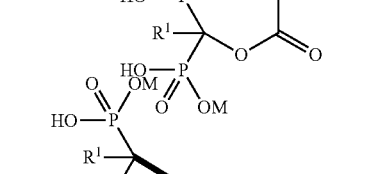

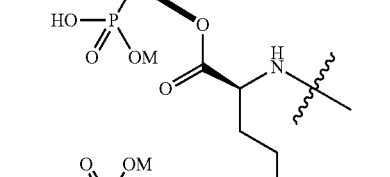

(VIIIb)

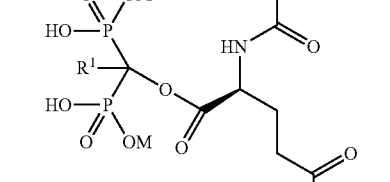

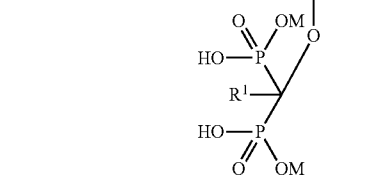

wherein
R¹ may be the same or different and is independently selected from the group consisting of H, F, Cl, Br, I, $NO_2$, CN, $COOCH_3$, —CHO, —$CHOCH_3$, an $C_{1-8}$ alkyl group and an $C_{1-6}$ aryl group, and
M is independently selected from hydrogen, sodium, potassium, calcium, magnesium, ammonium and 2-ammonium-2-hydroxymethyl-propane-1,3-diol.

In the above prodrug of general formula (I), it is also preferred that the unit (c) is selected from one of the following structures (IX) to (XII):

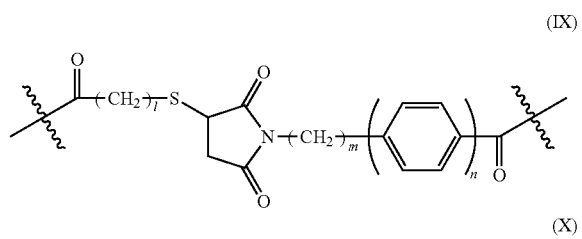
(IX)

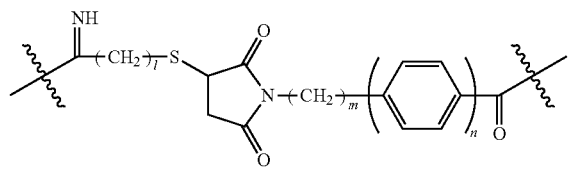
(X)

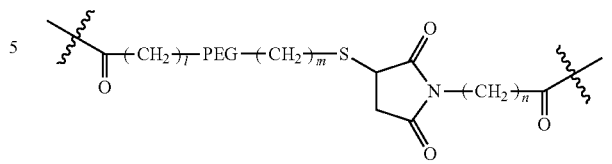
(XI)

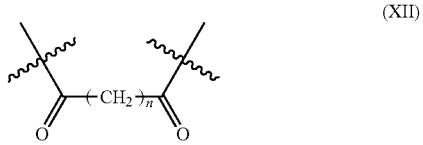
(XII)

In the above structures (IX) to (XII), l, m and n are independently selected from an integer of from 0 to 12. In above structures (IX) and (X), m is preferably 0, when n is an integer of from 1 to 12, and n is preferably 0, when m is an integer of from 1 to 12. In above structures (IX) and (X), it is particularly preferred that l is 3, m is 5 and n is 0. In above structure (XI), PEG represents poly(ethylene glycol), l and m are preferably 2, and n is preferably 5.

In the above prodrug of general formula (I), it is further preferred that the units (a) and (b) taken together are selected from one of the following structures (XIII) to (XVII):

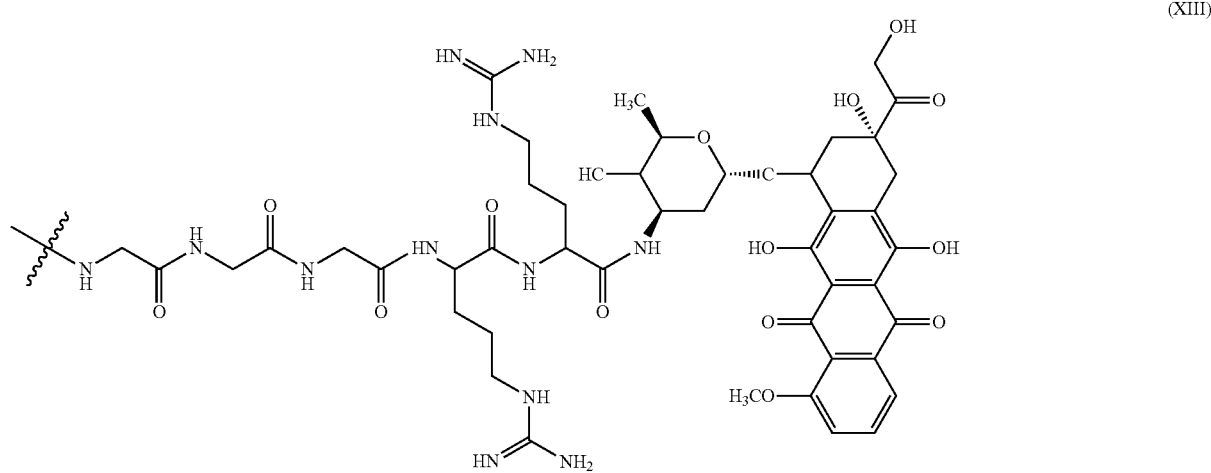
(XIII)

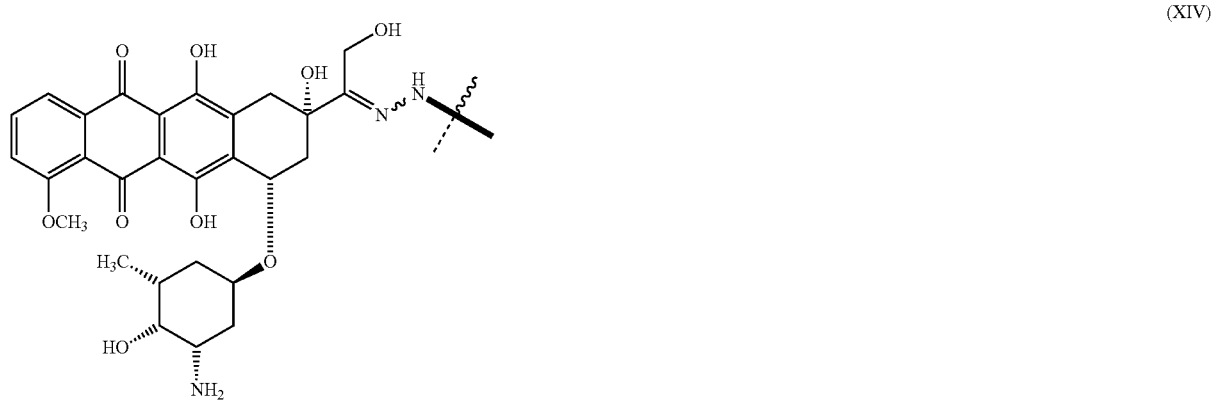
(XIV)

-continued
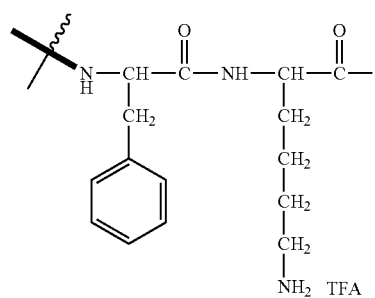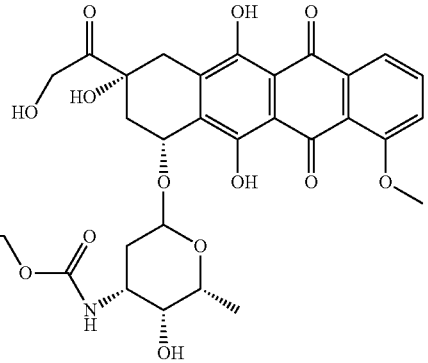
(XV)
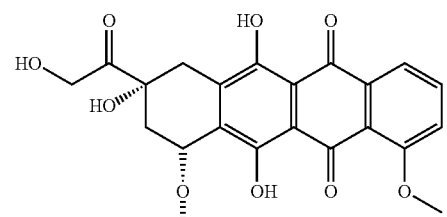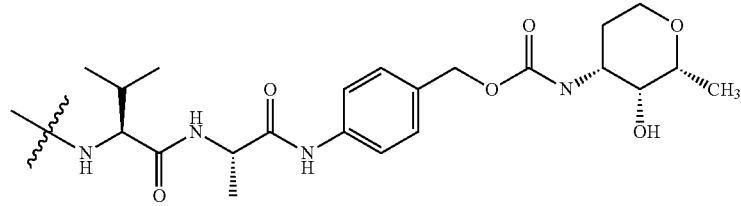
(XVI)
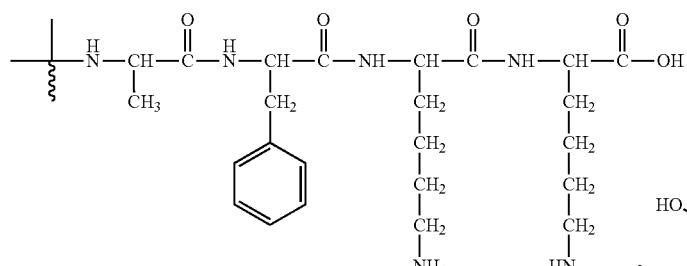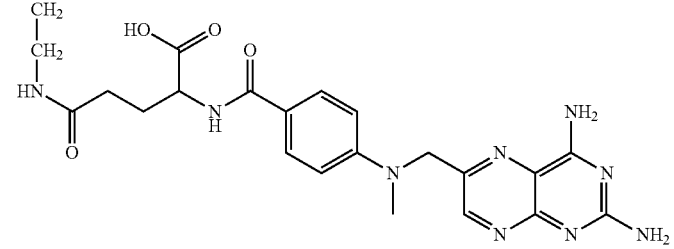
(XVII)

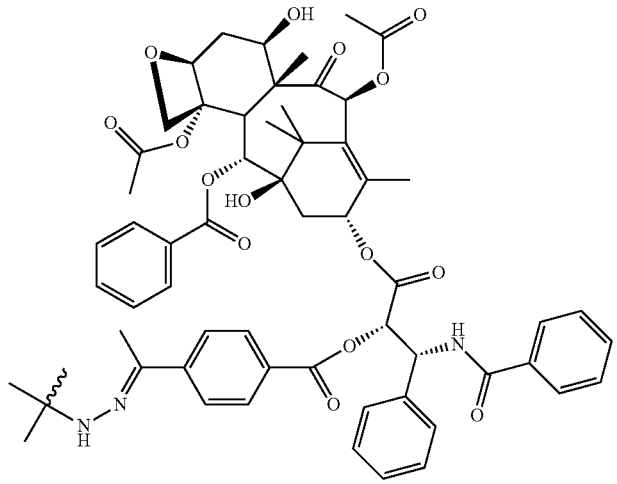
(XVIII)

In above unit (XIII), the cleavable linker comprises a Gly-Gly-Gly-Arg-Arg (SEQ ID NO:8) peptide sequence which can be cleaved by urokinase. In above units (XIV) and (XVIII), the cleavable linker comprises a hydrazone unit which is acid labile. In above unit (XV) and (XVI), the cleavable linker comprises a Phe-Lys and Val-Ala peptide sequence, respectively, which can be cleaved by cathepsin B.

Another aspect of the present invention relates to a pharmaceutical composition, comprising the prodrug as defined above, and optionally a pharmaceutically acceptable carrier and/or a pharmaceutically acceptable adjuvant and/or a diluent.

The pharmaceutical composition may for example contain solvents and diluents such as sodium chloride solution or a solution containing any pharmaceutically acceptable buffer. Moreover, the pharmaceutical composition of the present invention may be in any form suitable for administration to a patient, for example in an injectable form, as a tablette or a capsule, or as a composition for inhalation.

According to a specific embodiment, the above-defined pharmaceutical composition is used for the treatment of a bone-related disorder, in particular for the treatment of bone cancer including bone metastases.

According to another embodiment of the present invention, the prodrug as defined above may be comprised in a kit, which may further contain one or more adjuvants, such as a buffer or a pharmaceutically acceptable carrier.

The synthesis pathway of the prodrug of the present invention is not restricted. In one example, the prodrug of the present invention can be synthesized using a building block comprising a maleinimide group, the cleavable linker and the pharmaceutically and/or diagnostically active compound. The synthesis of said building block is known from the prior art (cf. for example D. E. Chung, F. Kratz, *Bioorg. Med. Chem. Lett.* 2006, 16, 5157-5163; F. Kratz, *Expert. Opin. Investig. Drugs* 2007, 16, 855-866).

The bisphosphonate can be prepared form tetraethyl methylene-bisphosphonate by first introducing a double bond and then an aliphatic side chain containing a free sulfhydryl group as shown in Examples 1 and 2 and then reacted with a maleimide-bearing prodrug.

FIG. 1 shows chromatograms of cleavage studies with compound 14 (Example 4(a)).

Figure 3:
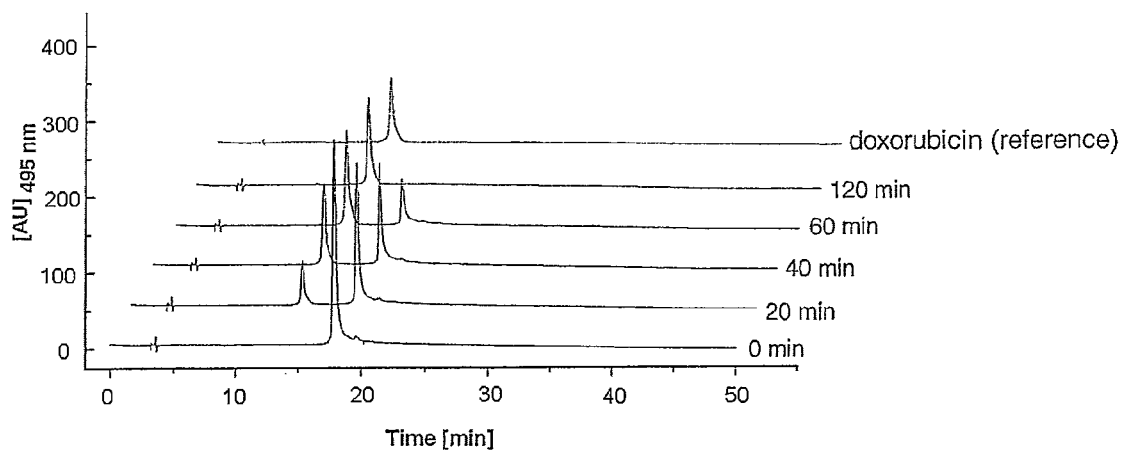

FIG. 3 shows chromatograms of cleavage studies with compound 23 (Example 4(c)). In particular, chromatograms of an incubation study of compound 23 at pH 5.0 and 37° C. with cathepsin B are shown. The cleavage product doxorubicin is included as reference.

Figure 4:
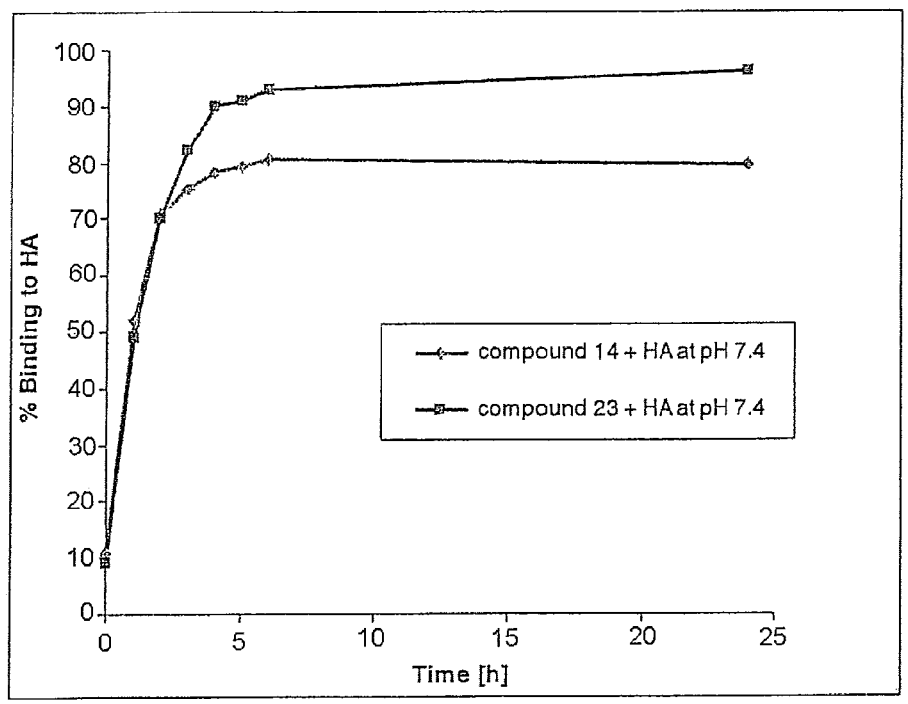

FIG. 4 shows the binding of prodrug 14 and 23 to hydroxyapatite (HA) at pH 7.4 and 37° C.

Figure 5:
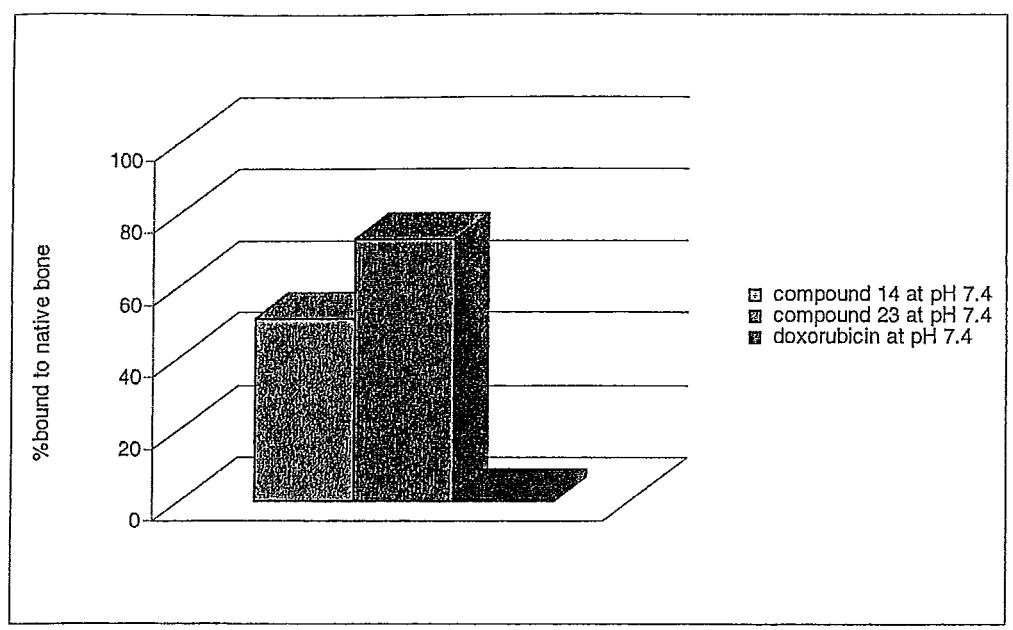

FIG. 5 shows binding studies of bisphosphonate prodrugs 14 and 23 and doxorubicin to native bone after 4 h at 37° C. and at pH 7.4.

According to the present invention, novel target-directed prodrugs are provided which advantageously show an accelerated and specific release of pharmaceutically and/or diagnostically active compounds contained therein when the prodrug is cleaved preferably at the desired site of action. Therefore, a highly improved drug release is advantageously achieved, which is connected to a high efficacy of e.g. a cytostatic treatment of bone disorders such as bone cancer, when compared to the state of the art. Thus, an improved treatment of e.g. bone metastases of a cancer patient is possible, wherein the cytostatic agent contained in the prodrug exhibits less side effects.

The present invention is illustrated in the following examples without any limitations thereto.

EXAMPLE 1

The synthesis of a bisphosphonate prodrug based on a doxorubicin prodrug, the 6-maleimidocaproylhydazone derivative of doxorubicin (DOXO-EMCH) and (3-mercaptopropylthio)ethylene-bisphosphonic acid is described below. DOXO-EMCH is an acid-sensitive thiol-binding drug and it is cleavable at pH 5.0 and releases doxorubicin (F. Kratz et al., *J. Med. Chem.* 2002, 45, 5523-5533).

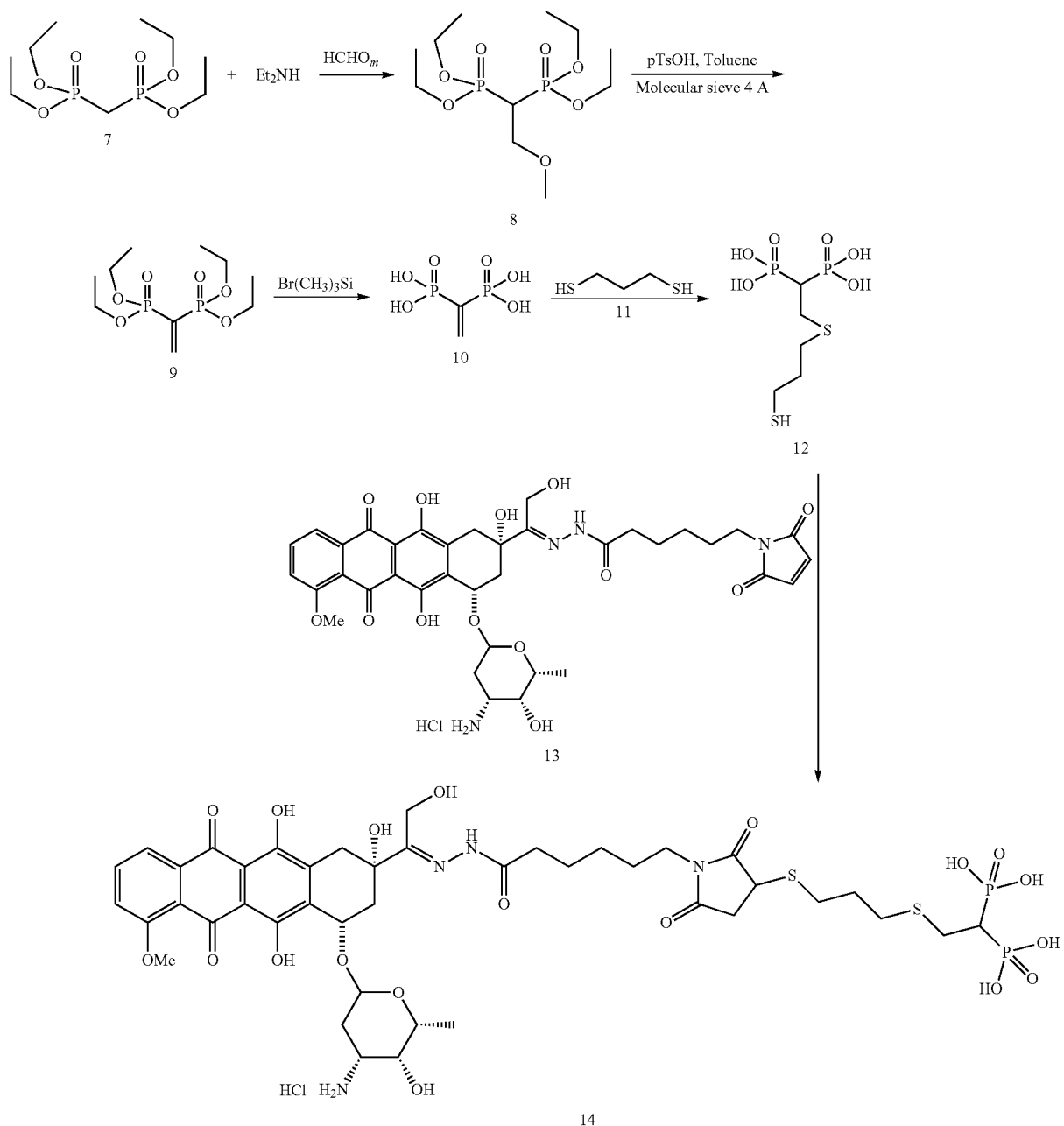

A suspension of diethylamine (2.28 mL, 21.91 mmol, 1 eq) and paraformaldehyde (3.29 g, 109.56 mmol, 5 eq) in 65 mL methanol was warmed until it became a colorless solution. The mixture was cooled to room temperature and tetraethyl methylene-bisphosphonate 7 was added. Then, the reaction mixture was refluxed for 24 h, and the solvent was removed under reduced pressure. The residue was dissolved in toluene and the solution was concentrated and dried in vacuo to yield 6.0 g (82%) of 8 as a colorless oil.

$^1$H NMR (400 MHz, CDCl$_3$) of compound 8: δ[ppm] 1.34 (t, 12H, J=7.1 Hz), 2.69 (tt, 1H, J=11.0 Hz, J=23.8 Hz), 3.37 (s, 3H), 3.89 (td, 2H, J=5.5 Hz, J=16.2 Hz), 4.14-4.21 (m, 8H). $^{13}$C NMR (125 MHz, CDCl$_3$): δ[ppm] 16.3, 16.4, 38.8 (t, J=132.6 Hz), 58.7, 62.6 (t, J=6.6 Hz), 68.0.

In the next step 2.2 g of tetraethyl 2-methoxyethylene-bisphosphonate 8 (6.62 mmol, 1 eq) was diluted in 150 mL anhydrous toluene and 0.18 g p-toluene sulfonic acid (0.97 mmol, 0.15 eq) was added. The reaction mixture was refluxed using a soxhlet apparatus containing molecular sieve 4 Å overnight, and the solvent was removed under reduced pressure to obtain slightly yellow oil. After addition of 50 mL CCl$_4$ to the crude product, the solution was washed with water (3×30 mL) and the aqueous layer was dried in vacuo by lyophilisation. Compound 9 was obtained as colorless oil (1.68 g, 85%).

$^1$H NMR (400 MHz, CDCl$_3$) of compound 9: δ[ppm] 1.33 (t, 12H, J=7.1 Hz), 4.07-4.18 (m, 8H), 6.97 (dd, 2H, J=33.8 Hz, J=35.8 Hz). $^{13}$C NMR (125 MHz, CDCl$_3$): δ[ppm] 16.2, 62.6, 132.0 (t, J=166.5 Hz), 149.2. $^{31}$P NMR: δ[ppm] 13.0.

To hydrolyze the bisphosphonate esters, 9 (0.97 g, 3.02 mmol, 1 eq) was diluted in anhydrous $CH_2Cl_2$ (20 mL), and the solution was cooled to 0° C. Then, trimethylsilylbromide (4.39 mL, 33.23 mmol, 11 eq) was added drop-wise. The solution was warmed to room temperature and stirred for 48 h. After removing the solvent under reduced pressure, methanol (15 mL) was added, and the mixture was stirred for 20 min at room temperature. Finally, the solvent was evaporated and the residue was dried in vacuo to yield compound 10 as a yellow oil. The crude product was used in the next step without any further purification.

Under $N_2$ atmosphere 0.84 g of the crude product 10 (4.49 mmol, 1 eq) was diluted with 5 mL 1-butanol, 1,3-propanedithiol 11 was added and the solution was heated under reflux for 3.5 h. The mixture was cooled to room temperature, and 30 mL $H_2O$ was added. This solution was extracted with hexane (4×20 mL) and the aqueous layer was lyophilized to obtain 12 as a colorless solid (0.84 g, 94%).

$^1$H NMR (400 MHz, $D_2O$) of compound 12: δ[ppm] 1.77 (p, 2H, J=7.1 Hz), 2.43 (tt, 1H, J=6.5 Hz, J=23.0 Hz), 2.50 (t, 2H, J=7.0 Hz), 2.59 (t, 2H, J=7.1 Hz), 2.90 (td, 2H, J=6.4 Hz, J=16.0 Hz). $^{13}$C NMR (125 MHz, $D_2O$): δ[ppm] 22.5, 27.0 (t, J=4.3 Hz), 30.2, 32.2, 39.1 (t, J=124.1 Hz). $^{31}$P NMR: δ[ppm] 19.7. MS (ESI): m/z 295 (M−H)$^+$.

In the last step, 21.44 mg (3.5 mmol) DOXO-EMCH 13 dissolved in 8 mL 10 mM sodium phosphate buffer (pH 7.4) and tert-butanol (1:1) was added drop-wise to 9.5 mg 12 dissolved in 8 mL 50 mM sodium phosphate buffer (pH 7.4) at room temperature and the sample was stirred for 5 min. The solvent was removed in high vacuum yielding 70 mg 14 as a red powder. The purity was measured on a Synergi MAX-RP 4 μm (4.6×250 mm) HPLC using 15% acetonitrile and 85% 20 mM sodium phosphate buffer (pH 7.0) as mobile phase A and 30% acetonitrile and 70% 20 mM sodium phosphate buffer (pH 7.0) as mobile phase B. The gradient was 0 to 35 min to 100% phase B, 35 to 40 min to phase A. Flow 1 mL/min.

The Mass spectrum showed the main peak for the product without the aglycone MS (ESI): m/z 916.2 (M−H)$^+$.

EXAMPLE 2

The synthesis of a bisphosphonate doxorubicin prodrug, EMC-Phe-Lys-PABC-Doxo (15) (EMC=6-maleimidocaproic acid; doxo=doxorubicin; PABC=para-aminobenzyloxycarbonyl) which is cleaved by cathepsin B and (3-mercaptopropylthio)ethylene-bisphosphonic acid 12, which was synthesized in four steps (see above), is depicted below:

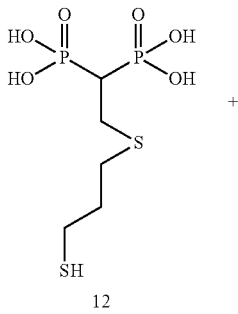

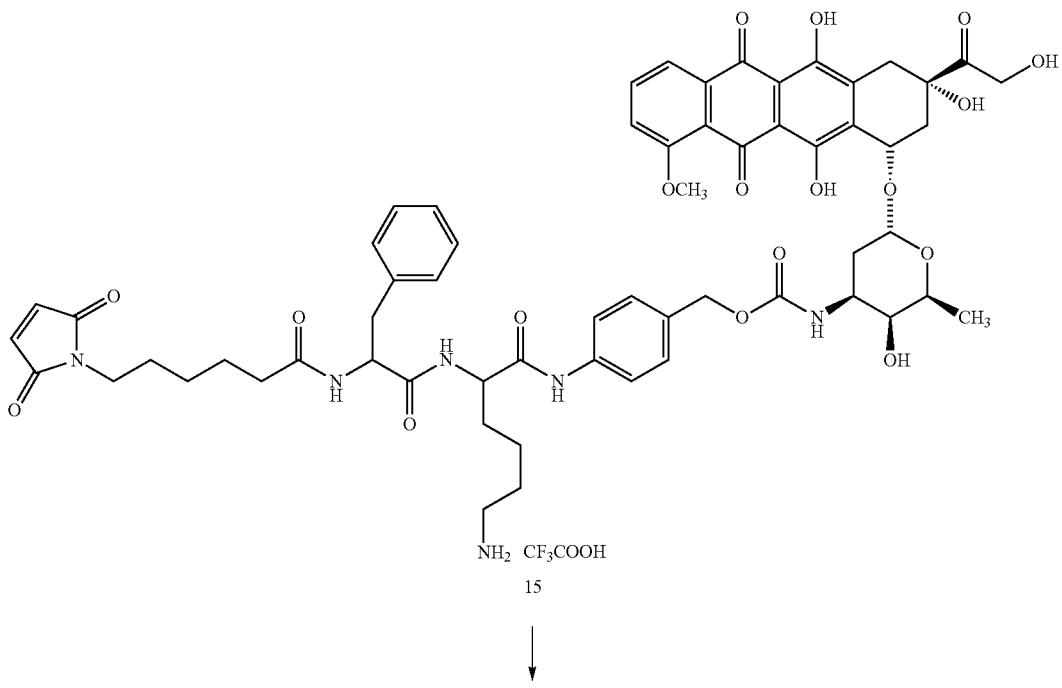

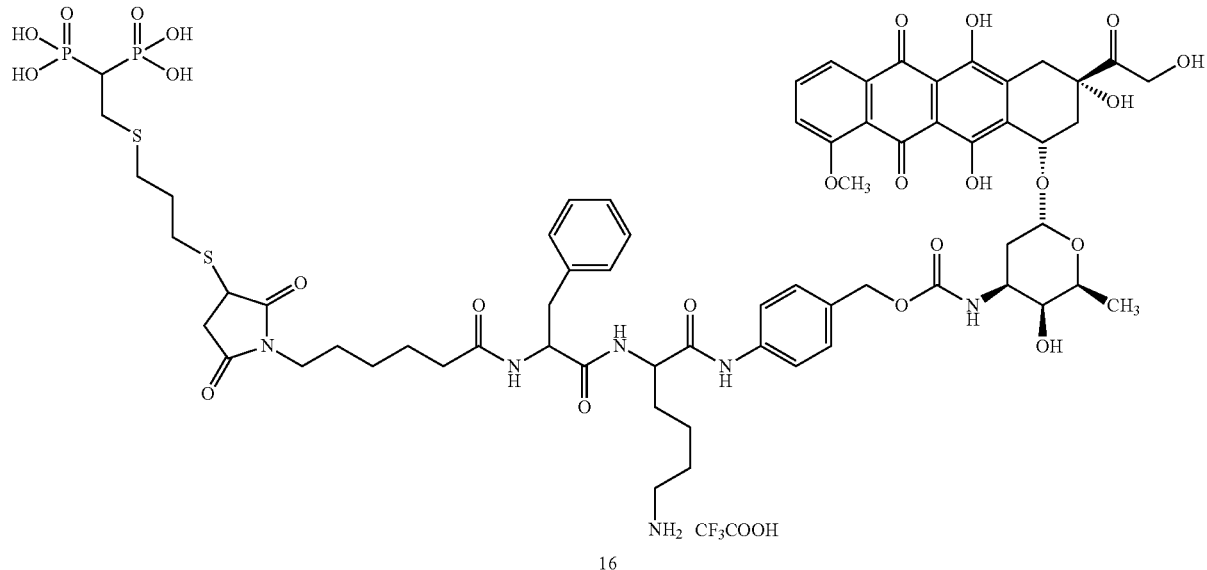

16

In the last step, 60 mg (3.4 mmol) EMC-Phe-Lys-PABC-Doxo 15 dissolved in 14 mL ethanol was added drop-wise to a solution of 16.7 mg 12 (3.4 mmol) dissolved in 14 mL 50 mM sodium phosphate buffer (pH 7.4) at 37° C., and the sample was stirred for 30 min. The solvent was centrifuged and the solvent removed in high vacuum yielding 140 mg 16 as a red powder. The purity was measured on a Synergi MAX-RP 4 μm (4.6×250 mm) HPLC using 15% acetonitrile and 85% 20 mM sodium phosphate buffer (pH 7.0) as mobile phase A and 30% acetonitrile and 70% 20 mM sodium phosphate buffer (pH 7.0) as mobile phase B. The gradient was 0 to 35 min to 100% phase B, 35 to 40 min to phase A. Flow 1 mL/min. MS (ESI): m/z 1457 (M+H)$^+$.

EXAMPLE 3

The synthesis of a bisphosphonate doxorubicin prodrug, EMC-Val-Ala-PABC-Doxo (18), which is cleaved by cathepsin B and (3-mercaptopropylthio)ethylene-bisphosphonic acid 12, which was synthesized in four steps (see above), is depicted below:

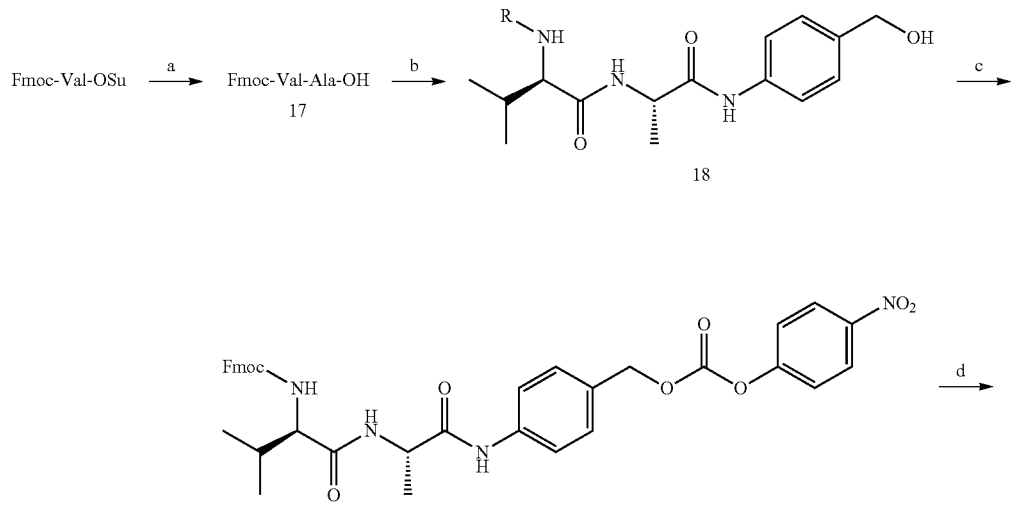

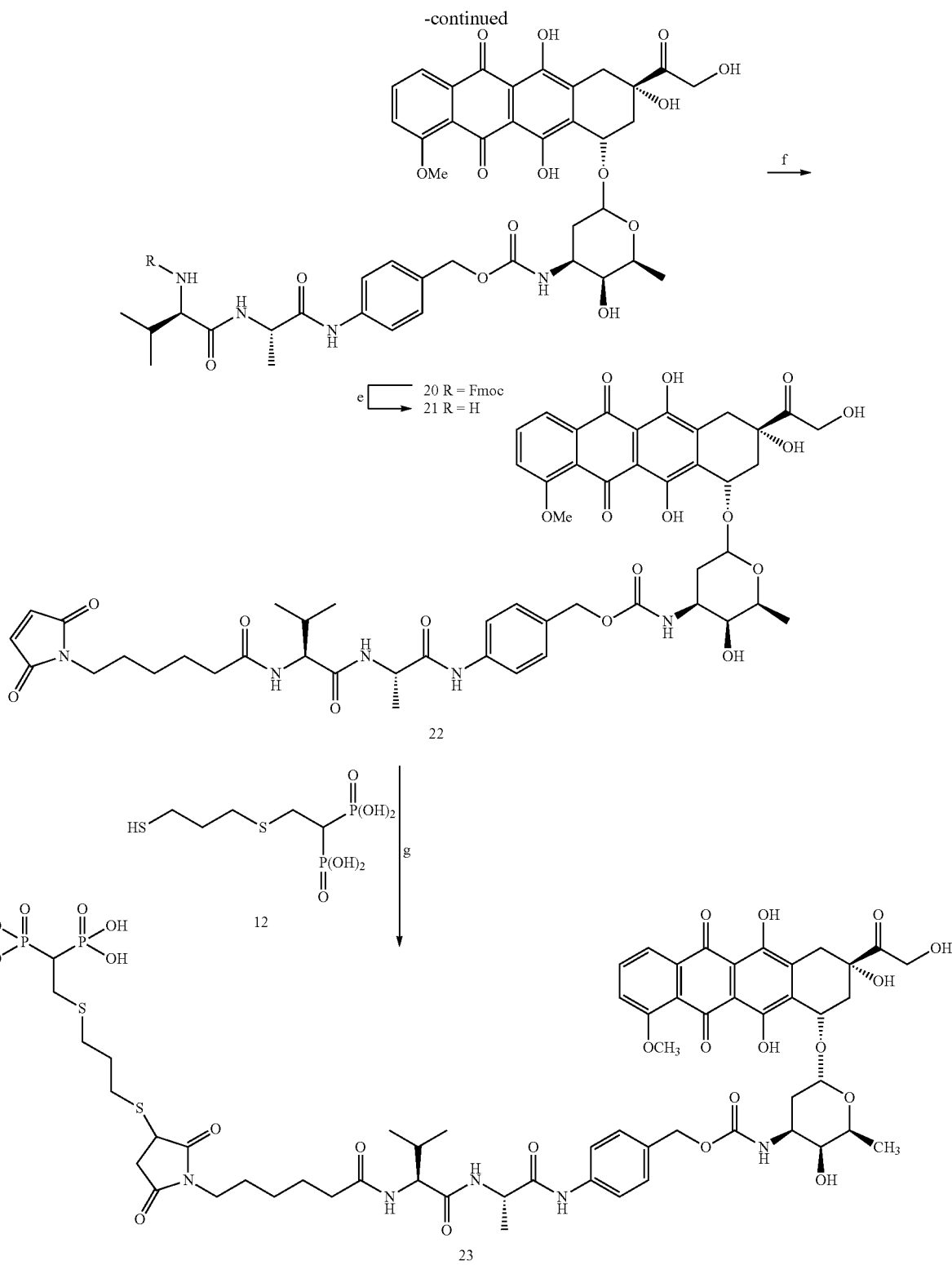
Reagents and conditions:
a: H-Ala-OH, NaHCO₃, H₂O, THF, RT
b: PABOH, EEDQ, DCM, RT
c: DIPEA, bis-PNP carbonate, DCM, DMF, RT
d: doxorubicin-HCl, DIPEA, DMF, RT
e: piperidin in 20% DMF, RT
f: DMF, DCM, EMC-OSu, RT
g: NH₄HCO₃ buffer (pH 7.4)

The doxorubicin prodrug 22, EMC-Val-Ala-PABC-Doxo, was synthesized in six steps, which is described below.

2.0 g of Fmoc-Val-OSu (4.58 mmol, 1 eq) diluted in 10 mL THF was added to a solution of 0.43 g H-Ala-OH (4.81 mmol, 1.05 eq) and a solution of 0.40 g NaHCO$_3$ (4.81 mmol, 1.05 eq) dissolved in 15 mL H$_2$O. Immediately, the colorless solution turned turbid. A mixture of H$_2$O, THF and diethyl ether (60 mL, 1:1:1) was added until a clear solution resulted. The solution was stirred well at room temperature. After a week the solvents were removed under reduced pressure and 30 mL citric acid (15% aqueous) and 50 mL ethyl acetate were added and the mixture was stirred for one hour at room temperature. The phases were separated and the aqueous layer was extracted three times (3×100 mL) with ethyl acetate. The combined organic phases were dried, and the solvent was evaporated. Afterwards, the residue was purified by flash chromatography on silica gel (CHCl$_3$/MeOH 30:1+1% AcOH) to give a colorless solid (1.60 g, 85%).

$^1$H NMR (DMSO-d$_6$): δ[ppm] 0.87 (d, 3H, J=6.8 Hz), 0.90 (d, 3H, J=6.8 Hz), 1.27 (d, 3H, J=7.3 Hz), 1.94-2.06 (m, 1H), 3.90 (t, 1H, J=7.2 Hz), 4.17-4.31 (m, 4H), 7.30-7.35 (m, 2H), 7.39-7.44 (m, 3H), 7.76 (t, 2H, J=6.6 Hz), 7.89 (d, 2H, J=7.5 Hz), 8.22 (d, 1H, J=6.9 Hz), 12.50 (bs, 1H). $^{13}$C NMR (DMSO-d$_6$): δ[ppm] 17.5, 18.6, 19.6, 30.9, 47.1, 47.9, 60.2, 66.1, 120.5, 125.8, 127.5, 128.1, 141.1, 144.2, 144.3, 156.5, 171.4, 174.4.

Under an inert gas atmosphere a suspension of 0.36 g Fmoc-Val-Ala-OH 17 (0.88 mmol, 1 eq), 0.13 g 4-aminobenzyl alcohol (1.06 mmol, 1.2 eq) and 0.33 g EEDQ (1.33 mmol, 1.5 eq) in dichloromethane was treated with methanol until a clear solution resulted. During the next two days a precipitate was formed. After filtration, the precipitate was washed with diethyl ether and sonicated for 15 min at room temperature. This procedure was repeated twice and the product 18 was dried in high vacuo (0.29 g, 64%).

$^1$H NMR (DMSO-d$_6$): δ[ppm] 0.86 (d, 3H, J=6.8 Hz), 0.90 (d, 3H, J=6.8 Hz), 1.31 (d, 3H, J=7.1 Hz), 1.96-2.04 (m, 1H), 3.92 (t, 1H, J=7.2 Hz), 4.21-4.34 (m, 3H), 4.40-4.46 (m, 3H), 5.11 (t, 1H, J=5.7 Hz), 7.24 (d, 2H, J=8.5 Hz), 7.33 (t, 2H, J=7.4 Hz), 7.40-7.47 (m, 3H), 7.54 (d, 2H, J=8.4 Hz), 7.75 (t, 2H, J=7.1 Hz), 7.89 (d, 2H, J=7.5 Hz), 8.17 (d, 1H, J=7.0 Hz), 9.93 (bs, 1H). $^{13}$C NMR (DMSO-d$_6$): δ[ppm] 18.6, 18.7, 19.6, 30.8, 47.1, 49.4, 60.4, 63.0, 66.1, 119.3, 120.5, 125.8, 127.3, 127.5, 128.0, 128.1, 137.8, 138.0, 141.1, 144.2, 144.3, 156.6, 171.3, 171.4.

Under a nitrogen atmosphere 4.2 mL N,N-diisopropylethylamine (DIPEA) (24.55 mmol, 3 eq) was added to a suspension of Fmoc-Val-Ala-PABOH 18 (4.22 g, 8.18 mmol, 1 eq) and bis-PNP carbonate (3.73 g, 12.28 mmol, 1.5 eq) in dry dichloromethane (84 mL). This yellow mixture was treated with 42 mL dry N,N-dimethylformamide (DMF) until a clear solution resulted and stirred over night at room temperature. Then, the solution was washed with water (60 mL) and the phases were separated. The aqueous layer was extracted four times with dichloromethane (a 30 mL) and the combined organic phases were dried and the solvent was removed under reduced pressure. The oily yellow residue was treated with diethyl ether (30 mL), sonicated and the precipitate was dried in vacuo to isolate product 19 as a white solid (4.1 g, 74%).

$^1$H NMR (DMSO-d$_6$): δ[ppm] 0.87 (d, 3H, J=6.8 Hz), 0.90 (d, 3H, J=6.7 Hz), 1.32 (d, 3H, J=7.0 Hz), 1.96-2.05 (m, 1H), 3.94 (t, 1H, J=7.3 Hz), 4.21-4.34 (m, 3H), 4.45 (p, 1H, J=7.0 Hz and 13.8 Hz), 5.25 (s, 2H), 7.31-7.47 (m, 7H), 7.55-7.77 (m, 6H), 7.89 (d, 2H, J=7.5 Hz), 8.21 (d, 1H, J=6.9 Hz), 8.30-8.33 (m, 2H), 10.10 (s, 1H). $^{13}$C NMR (DMSO-d$_6$): δ[ppm] 18.4, 18.7, 19.6, 30.8, 47.1, 49.5, 60.4, 66.1, 70.7, 119.5, 120.5, 123.6, 125.8, 126.6, 127.5, 128.1, 129.9, 139.9, 141.1, 144.2, 144.3, 145.6, 152.4, 155.7, 156.6, 171.5, 171.7.

Under a nitrogen atmosphere compound 19 (Fmoc-Val-Ala-PABC-PNP, 89 mg, 0.13 mmol, 1.1 eq), doxorubicin-.HCl (69 mg, 0.12 mmol, 1 eq) and DIPEA (20 μL, 0.12 mmol, 1 eq) were dissolved in 2 mL DMF (abs.) and stirred over night at room temperature. The crude product was precipitated dropwise with a mixture of diethyl ether and hexane (5:1, 100 mL) over 5 min. The precipitate was centrifuged, washed twice with diethyl ether and dried in vacuo. This crude product 20 (130 mg) was used in the next step without further purification.

20 (130 mg, 0.12 mmol, 1 eq) was dissolved in 3 mL piperidine (20% in DMF) and stirred for 10 min at room temperature. The product was precipitated with a mixture of diethyl ether and hexane (100 mL, 4:1) and was then purified by flash chromatography (CHCl$_3$/MeOH 30:1). After removal of the solvent, product 21 was obtained in a yield of 49% over two steps (51 mg).

Under nitrogen H$_2$N-Val-Ala-PABC-DOXO 21 (0.44 g, 0.51 mmol, 1 eq) was dissolved in a mixture of dichloromethane (abs.) and dry N,N-dimethylformamide (5:1, 42 mL). After addition of 234 mg 6-maleimimidocaproic acid N-hydroxysuccinimide ester (EMC-OSu) (0.76 mmol, 1.5 eq), the solution was treated with 71 μL triethylamine (0.51 mmol, 1 eq) and stirred for 18 h at room temperature. The crude product was precipitated with a mixture of 600 mL hexane and 100 mL diethyl ether. The red solid was washed twice with ether, dried in vacuo and purified by flash chromatography (CHCl$_3$/MeOH 31:1) on silica gel to give the product 22 as a red solid (213 mg, 40%).

HPLC analysis was carried out with a Waters Symmetry 300 Å C18 5 μm [4.6×250 mm] with pre-column [3.9×20 mm]; chromatographic conditions: flow: 1.0 mL/min, mobile phase A: 15% CH$_3$CN, 85% 20 mM sodium phosphate buffer (pH 7.0); mobile phase B: 30% CH$_3$CN, 70% 20 mM sodium phosphate buffer (pH 7.0); injection volume: 50 μL; gradient: 0-1.5 min 100% mobile phase A; 1.5-20 min increase to 30% CH$_3$CN, 70% 20 mM sodium phosphate buffer; 20-45 min 70% CH$_3$CN, 30% 20 mM sodium phosphate buffer; 45-55 min decrease to initial mobile phase; 55-58 min 100% mobile phase A. C$_{53}$H$_{61}$N$_5$O$_{18}$, HRMS ESI-TOF: calculated [M+Na]$^+$ 1078.39. found 1078.2.

In the last step, 35 mg of compound 12 was dissolved with 29 mL 50 mM ammonium bicarbonate buffer (pH 7.4) to obtain a thiol concentration of 3.2 mM. A solution of 99 mg EMC-Val-Ala-PABC-DOXO 22 dissolved in 40 mL 10 mM ammonium bicarbonate buffer (pH 7.4, 3.2 mM) was added dropwise to the bisphosphonate solution over 5 min. The mixture was stirred well at room temperature for 15 min and was freezed with liquid nitrogen. After lyophilization, the red crude product was purified by flash chromatography (RP 18) eluting with CH$_3$CN/H$_2$O(HPLC grade) 1:1 to give 23 as a red solid. HPLC analysis was carried out with a Waters Symmetry 300 Å C18 5 μm [4.6×250 mm] with pre-column [3.9× 20 mm]; chromatographic conditions: flow: 1.2 mL/min, mobile phase A: 20% CH$_3$CN, 80% 20 mM sodium phosphate buffer (pH 7.0); mobile phase B: 70% CH$_3$CN, 30% 20 mM sodium phosphate buffer (pH 7.0); injection volume: 20 μL; gradient: 0-5 min 100% mobile phase A; 5-40 min increase to 70% CH$_3$CN, 30% 20 mM sodium phosphate buffer; 40-50 min 70% CH$_3$CN, 30% 20 mM sodium phosphate buffer; 50-60 min decrease to initial mobile phase; 60-65 min 100% mobile phase A. C$_{58}$H$_{75}$N$_5$O$_{24}$P$_2$S$_2$, HRMS ESI-TOF: calculated [M−H]$^-$ 1350.3640. found 1350.3772.

EXAMPLE 4

Cleavage Studies with Compounds 14, 16 and 23

(a) Cleavage Studies with Compound 14

1 mL of a 300 µM solution of 14 in 50 mM sodium phosphate buffer was prepared and a 50 µL sample was analyzed by reverse phase HPLC (see FIG. 1A). To 400 µL of this solution was added 4 µL concentrated phosphoric acid resulting in a pH value of 3.8. After 5 min at room temperature, a 50 µL sample was analyzed by reverse phase HPLC (see FIG. 1B) which showed that rapid cleavage to doxorubicin had taken place as shown by a comparison with pure doxorubicin as a reference (see FIG. 1C).

(b) Cleavage Studies with Compound 16

For cleavage of 16 with cathepsin B, 150 µL of a 50 mM sodium acetate buffer containing 100 mM NaCl, 4 mM EDTA $Na_2$ and 0.15 mg L-cysteine (pH 5.0). 6.7 µL cathepsin B solution (23.8 U/mg, from Calbiochem, Germany) were added to a 100 µL solution of 16 (300 µM in 50 mM sodium phosphate buffer, pH 7.0) and the solution incubated for 1 h at 37° C.

Figure 2B:
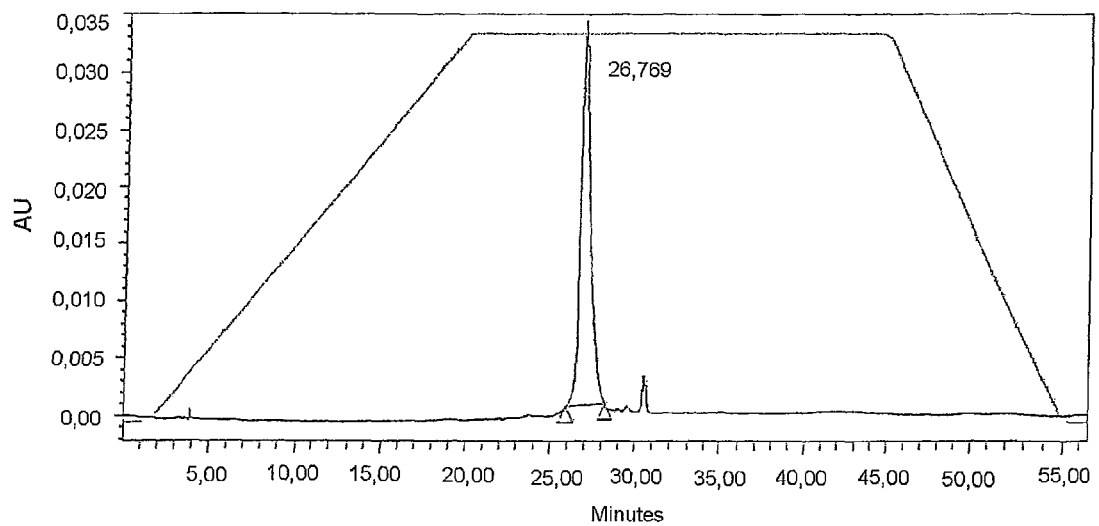
FIG. 2 shows chromatograms of cleavage studies with compound 16 (Example 4(b)).
Figure 2C:
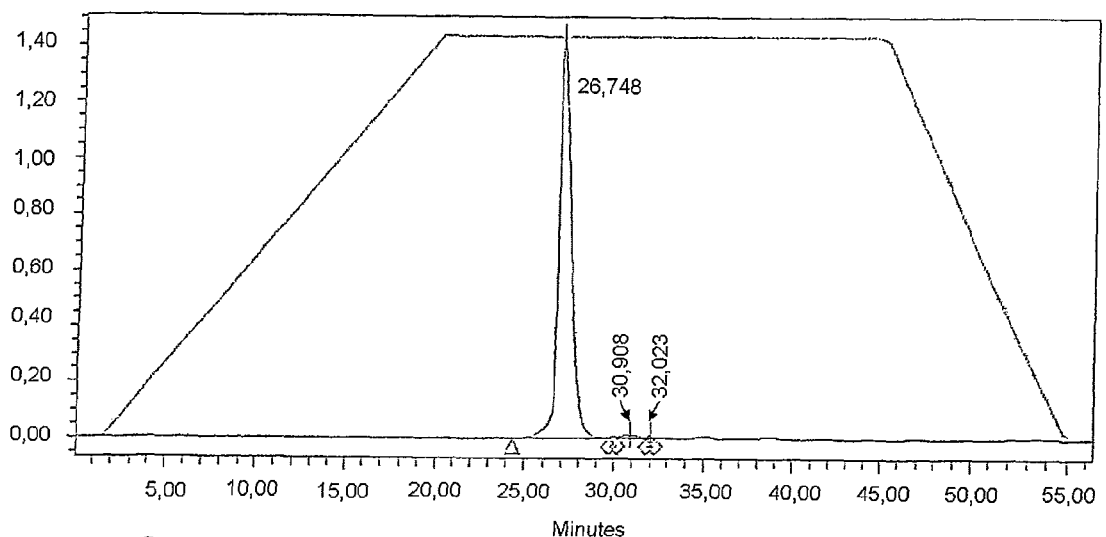

FIG. 2A shows the chromatograms at t=0 h with 16 eluting at ~45.7 min (50 µL injection). After an incubation time of 1 h a 50 µL sample was analyzed by reverse phase HPLC (see FIG. 2B) showing that complete cleavage to doxorubicin had taken place as shown by a comparison with pure doxorubicin as a reference (see FIG. 2C).

HPLC was carried out with a Symmetry300, C18, 5 µm (4.6×250 mm) HPLC using 15% acetonitrile and 85% 20 mM sodium phosphate buffer (pH 7.0) as mobile phase A and 30% acetonitrile and 70% 20 mM sodium phosphate buffer (pH 7.0) as mobile phase B. The gradient was 0 to 1.5 min 100% phase A, 1.5 to 20 min to 100% B, 20 min to 45 min 100% B, 45 to 55 min to 100% A. Flow 1 mL/min; injection volume: 50 µL.

(c) Cleavage Studies with Compound 23

A 176 µL stock solution of compound 23 [1.5 mM] was diluted with 9 µL cathepsin B (0.4 mg/mL, 23.8 U/mg, from Calbiochem, Germany) and 264 µL of buffer (50 mM sodium acetate, 100 mM NaCl, 4 mM EDTA, pH 5.0) containing L-cysteine (8 mM). The mixture was incubated at 37° C. and aliquots (65 µL) were taken after 0 min, 20 min, 40 min, 60 min and 120 min and analyzed by HPLC.

HPLC was carried out on a Symmetry300 C18 5 µm [4.6× 250 mm] with pre-column [3.9×20 mm]; chromatographic conditions: flow: 1.2 mL/min, mobile phase A: 20% $CH_3CN$, 80% 20 mM sodium phosphate buffer (pH 7.0); mobile phase B: 70% $CH_3CN$, 30% 20 mM sodium phosphate buffer (pH 7.0); injection volume: 20 µL; gradient: 0-5 min 100% mobile phase A; 5-40 min increase to 70% $CH_3CN$, 30% 20 mM sodium phosphate buffer; 40-50 min 70% $CH_3CN$, 30% 20 mM sodium phosphate buffer; 50-60 min decrease to initial mobile phase; 60-65 min 100% mobile phase A.

FIG. 3 shows the chromatograms at t=0 min, 20 min, 40 min, 60 min and 120 min with 23 eluting at ~19 min (50 µL injection) After an incubation time of 2 h a 50 µL sample was analyzed by reversed phase HPLC (see FIG. 3) showing that complete cleavage to doxorubicin had taken place as shown by a comparison with pure doxorubicin as a reference (see FIG. 3).

EXAMPLE 5

Binding Studies of Compounds 14 and 23 to Hydroxyapaptite

General procedure: In a falcon tube, the test compound was diluted in phosphate-buffer (4 mM $Na_2HPO_4$ containing 150 mM NaCl, pH 7.4) to obtain a solution with a concentration of 300 µM. Hydroxyapatite (30 eq) was added and the suspension was stirred well and incubated at 37° C. Another solution of the samples without hydroxyapatite was used as control. In each case after 0 h, 1 h, 2 h, 3 h, 4 h, 5 h, 6 h and 20 h the samples were centrifuged (4000 rpm, duration: 60 sec, Heraeus® Megafuge® 1.0) and the absorbance of the supernatant was measured with a spectrophotometer at a wavelength of 495 nm ($\epsilon_{495}$(doxorubicin)=10 650 $M^{-1}$ $cm^{-1}$). Each result represents the arithmetic average of three measurements and percent HA binding was calculated.

As seen in FIG. 4, prodrug 14 and 23 bind rapidly to hydroxyapatite and already after one hour approximately 50% of both prodrugs are bound to hydroxyapatite at pH 7.4 and at 37° C. With time red color intensity of the supernatant decreased an a concomitant red staining of the original white hydroxyapatite powder was observed. For the cathepsin cleavable prodrug 23 binding after 5 h was over 90% and after 24 h essentially 100%. The acid sensitive prodrug 14 demonstrated a similar curve shape but saturation of HA binding occurred after 5 h with ~80% of 14 being bound to HA.

EXAMPLE 6

Binding Studies of Compounds 14 and 23 to Native Bone Matrix

For this binding assay, bovine bone fragments were cut into small pieces (6 mm×4 mm×1 mm). The bone pieces were left untreated, washed with water (bidest.) and with absolute ethanol and dried over night at room temperature. Then, in a falcon tube the prodrugs were dissolved in phosphate-buffer (4 mM $Na_2HPO_4$ containing 150 mM NaCl, pH 7.4) to obtain a concentration of 300 µM. Approximately 50 mg of an untreated bone piece was added to the clear red solution, and the samples were incubated under stirring at 37° C. After 4 h, the samples were centrifuged (4000 rpm, duration: 60 sec, Heraeus® Megafuge® 1.0), and the absorbance of the supernatant was measured with a spectrophotometer at a wavelength of 495 nm ($\epsilon_{495}$(doxorubicin)=10650 $M^{-1}$ $cm^{-1}$). Percent bone binding was calculated As a control, doxorubicin was used which was incubated with the bone fragments. As expected, no binding of doxorubicin to the native bone was observed (see FIG. 5). In contrast, 50-75° A, of both prodrugs were bound to the bone matrix after 4 h at pH 7.4 (FIG. 5).

---

The invention claimed is:
1. A prodrug selected from the group consisting of:
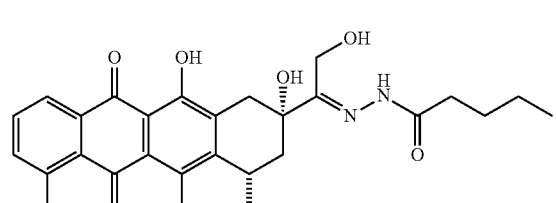
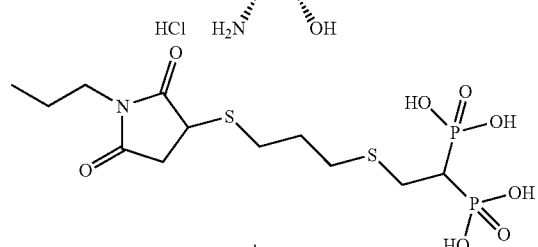
and
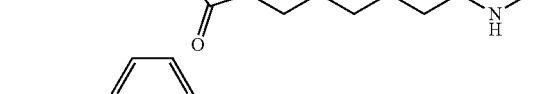
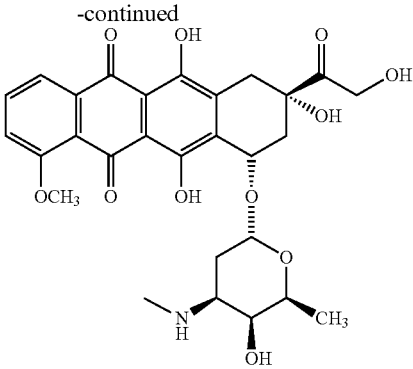
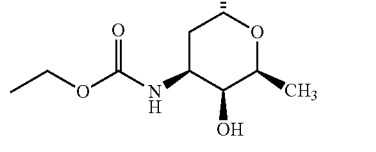
* * * * *